US010786505B2

(12) United States Patent
Berger et al.

(10) Patent No.: US 10,786,505 B2
(45) Date of Patent: Sep. 29, 2020

(54) ADMINISTRATION OF NEDD8-ACTIVATING ENZYME INHIBITOR AND CHEMOTHERAPEUTIC AGENTS

(71) Applicant: Millennium Pharmaceuticals, Inc., Cambridge, MA (US)

(72) Inventors: Allison Berger, Arlington, MA (US); Eric S. Lightcap, Natick, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/980,165

(22) Filed: May 15, 2018

(65) Prior Publication Data
US 2018/0325904 A1 Nov. 15, 2018

Related U.S. Application Data

(63) Continuation of application No. 14/889,571, filed as application No. PCT/US2014/037888 on May 13, 2014, now abandoned.

(60) Provisional application No. 61/822,994, filed on May 14, 2013, provisional application No. 61/874,393, filed on Sep. 6, 2013, provisional application No. 61/891,943, filed on Oct. 17, 2013.

(51) Int. Cl.
*A61K 31/519* (2006.01)
*A61K 31/282* (2006.01)
*A61K 31/337* (2006.01)
*A61K 31/555* (2006.01)
*A61K 31/7068* (2006.01)
*A61K 33/24* (2019.01)
*A61K 45/06* (2006.01)

(52) U.S. Cl.
CPC .......... *A61K 31/519* (2013.01); *A61K 31/282* (2013.01); *A61K 31/337* (2013.01); *A61K 31/555* (2013.01); *A61K 31/7068* (2013.01); *A61K 33/24* (2013.01); *A61K 45/06* (2013.01)

(58) Field of Classification Search
CPC ............................ C07D 493/08; A61K 31/519
USPC ........................................... 546/139; 514/649
See application file for complete search history.

(56) References Cited

U.S. PATENT DOCUMENTS

| | | | |
|---|---|---|---|
| 7,951,810 B2 | 5/2011 | Critchley et al. | |
| 8,207,177 B2 | 6/2012 | Langston et al. | |
| 8,980,850 B2 | 3/2015 | Smith | |
| 2011/0021544 A1 | 1/2011 | Armitage et al. | |
| 2012/0115892 A1* | 5/2012 | Dezube | A61K 9/0019 514/265.1 |
| 2012/0196823 A1 | 8/2012 | Tutino et al. | |

FOREIGN PATENT DOCUMENTS

| | | |
|---|---|---|
| WO | WO 2008/019124 A1 | 2/2008 |
| WO | WO 2012/061551 A1 | 5/2012 |
| WO | WO 2013/052814 A2 | 4/2013 |

OTHER PUBLICATIONS

Huang, Cancer Treatment Reviews 38 (2012) 613-617.*
Koeller, Cancer (1986), 57(2), 222-5.*
Pauer, Cancer Investigation, vol. 22, No. 6, pp. 886-896, 2004.*
Nawrocki, Expert Opinion on Investigational Drugs, Expert Opin. Investig. Drugs (2012) 21(10) 563-1573.*
Gao, Nature Cell Biology (2006), 8(10), 1171-1177.*
Marriott, Pharmaceutical Compound and Dispensing, Second Edition, 2010, 1-288.*
Ansel, Pharmaceutical Dosage Forms and Drug Delivery Systems, 1999, p. 48, 50, 51, 53.*
Bozic et al. eLife 2013;2:e00747, 1-15.*
Soucy, Nature, 458(9), 732-737, 2009.*
Marusyk, Biochimica et Biophysica Acta 1805 (2010) 105-117.*
Bauer, T.M., et al., "Investigational NEDD8-activating enzyme inhibitor pevonedistat plus chemotherapy in patients with solid tumors (phase 1b study): Activity of pevonedistat plus carboplatin/paclitaxel," Poster Presented at the American Society of Clinical Oncology (ASCO) Annual Meeting, Jun. 3-7, Chicago, IL, United States (2016).
Bhatia, S. et al., "MLN4924, an investigational NEDD8-activating enzyme (NAE) inhibitor, in patients (pts) with metastatic melanoma: Results of a phase I study," *J. Clin. Oncol.* 29(Suppl):Abstract 8529, American Society of Clinical Oncology, United States, 2 pages (2011).
Brownell, J.E., "Substrate-Assisted Inhibition of Ubiquitin-like Protein-Activating Enzymes: The NEDD8 E1 Inhibitor MLN4924 Forms a NEDD8-AMP Mimetic In Situ," *Mol. Cell* 37:102-111, Elsevier Inc., United States (2010).
Erba, H., et al., "MLN4924, a novel, investigational NEDD8-activating enzyme (NAE) inhibitor, in adult patients with acute myeloid leukemia (AML) or high-grade myelodysplastic syndromes (MDS): Results from a phase 1 study," *Haematologica* 96(s2):28, Abstract No. 0068, Ferrata-Storti Foundation, Italy (2011).
Extended European Search Report in European Patent Application No. 12844799.2, dated Aug. 26, 2015, European Patent Office, Munich, Germany, 6 pages.
Garcia-Manero, G., "Demethylating agents in myeloid malignancies," *Curr. Opin. Oncol.* 20(6):705-710, Lippincott Williams & Wilkins, United States (2008).
Garcia, K., et al., "Nedd8-Activating Enzyme Inhibitor MLN4924 Provides Synergy with Mitomycin C through Interactions with ATR, BRCA1/BRCA2, and Chromatin Dynamics Pathways," *Molecular Cancer Therapeutics* 13(6):1625-1635, American Association for Cancer Research, United States (2014).

(Continued)

Primary Examiner — Nizal S Chandrakumar
(74) Attorney, Agent, or Firm — Sterne, Kessler, Goldstein & Fox, P.L.L.C.

(57) ABSTRACT

Disclosed are methods for the treatment of various solid tumors in patients in need of such treatment. The methods comprise administering to such a patient an NEDD8-activating enzyme (NAE) inhibitor such as ((1S,2S,4R)-4-(4-((1S)-2,3-dihydro-1H-inden-1-ylamino)-7H-pyrrolo[2,3-d]-pyrimidin-7-yl)-2-hydroxycyclopentyl)methyl sulfamate (MLN4924) or a pharmaceutically acceptable salt in combination with one or more chemotherapeutic agents. Also disclosed are medicaments for use in the treatment of various solid tumors.

13 Claims, 4 Drawing Sheets

(56) References Cited

OTHER PUBLICATIONS

Harvey, R.D., "C15010: A Phase 1b, Open-Label, Dose Escalation, Multi-arm Study of MLN4924 Plus Docetaxel, Gemcitabine, or Combination of Carboplatin and Paclitaxel in Patients with Solid Tumors," Winship Clinical Trials, Emory University, accessed at https://oncore.emory.edu/sip/SIPControlServlet, accessed on Nov. 5, 2014, United States, 2 pages (2014).

International Search Report for International Application No. PCT/US2012/063382, dated Feb. 1, 2013, ISA/US, Commissioner for Patents, United States, 3 pages.

International Preliminary Report on Patentability and Written Opinion for International Application No. PCT/US2012/063382, dated Oct. 1, 2014, The International Bureau of WIPO, Geneva, Switzerland, 6 pages.

International Search Report for International Application No. PCT/US2014/037888, dated Dec. 8, 2014, ISA/US, Commissioner for Patents, United States, 5 pages.

International Preliminary Report on Patentability and Written Opinion for International Application No. PCT/US2014/037888, dated Nov. 17, 2015, The International Bureau of WIPO, Geneva, Switzerland, 17 pages.

Jacquemont, C., et al., "Non-specific chemical inhibition of the Fanconi anemia pathway sensitizes cancer cells to cisplatin," *Molecular Cancer* 11:26, BioMed Central, United States, 15 pages (2012).

Jänne, P.A., et al., "Selumetinib plus docetaxel for KRAS-mutant advanced non-small-cell lung cancer: a randomised, multicentre, placebo-controlled, phase 2 study," *Lancet Oncol*. 14(1):38-47, Lancet Publishing Group, England (2013).

Jazaeri, A.A., et al, "Overcoming Platinum Resistance in Preclinical Models of Ovarian Cancer Using the Neddylation Inhibitor MLN4924," *Mol Cancer Ther* 12(10):1958-1967, American Association for Cancer Research, Inc., United States (2013).

Katsumata, N., et al., "Dose-dense paclitaxel once a week in combination with carboplatin every 3 weeks for advanced ovarian cancer: a phase 3, open-label, randomised controlled trial," *Lancet* 374(9698):1331-1338, Lancet Publishing Group, England (2009).

Kauh, J.S., et al., "MLN4924, an investigational NEDD8-activating enzyme (NAE) inhibitor, in patients (pts) with advanced solid tumors: Phase I study of multiple treatment schedules," *J. Clin. Oncol*. 29(15):Abstract 3013, American Society of Clinical Oncology, United States, 2 pages.

Kee, Y., et al., "Inhibition of the Nedd8 System Sensitizes Cells to DNA Interstrand Cross-linking Agents," *Mol Cancer Res* 10(3):369-377, American Association for Cancer Research, United States (2012).

Lockhart, A.C., et al., "Phase 1b trial of investigational NEDD8-activating enzyme (NAE) inhibitor pevonedistat (TAK-924/MLN4924) in combination with docetaxel, paclitaxel/carboplatin, or gemcitabine in patients (pts) with solid tumors," Poster Presented at Proceedings of the AACR-NCI-EORTC International Conference: Molecular Targets and Cancer Therapeutics, Nov. 5-9, Boston, MA, 2 pages (2015).

Lockhart, A.C., et al., "Phase 1b trial of investigational NEDD8-activating enzyme (NAE) inhibitor pevonedistat (TAK-924/MLN4924) in combination with docetaxel, paclitaxel/carboplatin, or gemcitabine in patients (pts) with solid tumors," *Mol Cancer Ther* 14(12 Suppl 2):Abstract B26, American Association for Cancer Research, United States (2015).

McDonald, A., et al., "Pharmacodynamic assays demonstrate NAE pathway inhibition following administration of MLN4924 in patients with acute myeloid leukemia," *Haematologica* 97(s1):33, Abstract No. 0084, Ferrata-Storti Foundation, Italy (2012).

Milhollen, M., et al., "Treatment Emergent Mutations in NAEβ Confer Resistance to the NEDD8-Activating Enzyme inhibitor MLN4924 in pre-clinical AML and DLBCL models," *Blood* 118:Abstract 1413, American Society of Hematology, United States (2011).

Milhollen, M.A., "Azacitidine/Decitabine Synergism with the NEDD8-Activating Enzyme Inhibitor MLN4924 in Pre-Clinical AML Models," Poster Presented at the 53rd American Society of Hematology Meeting, Dec. 10-13, San Diego, CA, 14 slides (2011).

Milhollen, M.A., et al., "Treatment-Emergent Mutations in NAEβ Confer Resistance to the NEDD8-Activating Enzyme Inhibitor MLN4924," *Cancer Cell* 21:388-401, Elsevier Inc., United States (2012).

National Institutes of Health, "Effects of Fluconazole and Itraconazole CYP3A-Mediated Inhibition on the Pharmacokinetics, Safety, and Tolerability of MLN4924 in Patients With Advanced Solid Tumors," clinicaltrials.gov, ID No. NCT02122770, accessed at https://clinicaltrials.gov/ct2/show/NCT02122770, accessed on Apr. 10, 2017, 6 pages.

National Institutes of Health, "Dose Escalation, Multi-arm Study of MLN4924 Plus Docetaxel, Gemcitabine, or Combination of Carboplatin and Paclitaxel in Patients With Solid Tumors," clinicaltrials.gov, ID No. NCT01862328, accessed at https://clinicaltrials.gov/ct2/show/NCT01862328?term=NCT01862328&rank=1, accessed on Apr. 10, 2017, 4 pages.

Nawrocki, S.T., et al., "Disrupting NEDD8-Mediated Protein Turnover with MLN4924 Significantly Augments the Efficacy of Cytarabine," *Blood* 116:Abstract 3255, American Society of Hematology, United States, 2 pages (2010).

Nawrocki, S.T., et al., "Disrupting NEDD8-Mediated Protein Turnover with MLN4924 Significantly Augments the Efficacy of Cytarabine," Poster Presented at the 52nd American Society of Hematology Meeting, Dec. 4-7, Orlando, FL (2010).

Nawrocki, S.T., et al., "MLN4924: a novel first-in-class inhibitor of NEDD8-activating enzyme for cancer therapy," *Expert Opinion on Investigational Drugs* 21(10):1563-1573, Informa UK, Ltd., England (2012).

Partial Supplementary European Search Report, Communication pursuant to Rule 164(1) EPC, in European Patent Application No. 14797156.8, dated Jan. 2, 2017, European Patent Office, Munich, Germany, 7 pages.

Sen, S., et al., "Investigational NEDD8-Activating Enzyme (NAE) Inhibitor, MLN4924, Demonstrates Activity Against Primary AML Blast, Progenitor and Stem Cell Populations," *Blood* 118:Abstract 1414, American Society of Hematology, United States (2011).

Smith, P.G., et al., "Azacitidine/Decitabine Synergism with the NEDD8-Activating Enzyme Inhibitor MLN4924 in Pre-Clinical AML Models," *Blood* 118:Abstract 578, American Society of Hematology, United States (2011).

Soto Parra, H., et al., "Three-week versus four-week schedule of cisplatin and gemcitabine: results of a randomized phase II study," *Annals of Oncology* 13(7):1080-1086, Oxford University Press, England (2002).

Soucy, T.A., et al., "An inhibitor of NEDD8-activating enzyme as a new approach to treat cancer," *Nature* 458:732-736, Macmillan Publishers Limited, England (2009).

Soucy, T.A., et al., "Targeting NEDD8-Activated Cullin-RING Ligases for the Treatment of Cancer," *Clin. Cancer Res*. 15(12):3912-3916, American Association for Cancer Research, United States (2009).

Swords, R.T., et al., "MLN4924, A Novel First in Class Small Molecule Inhibitor of the Nedd8 Activating Enzyme (NAE), Has Potent Activity in Preclinical Models of Acute Myeloid Leukemia," *Blood* 114(22):Abstract 1021, American Society of Hematology, United States, 3 pages (2009).

Swords, R.T., et al., "MLN4924, A Novel First in Class Small Molecule Inhibitor of the Nedd8 Activating Enzyme (NAE), Has Potent Activity in Preclinical Models of Acute Myeloid Leukemia," 2010 SUMO, Ubiquitin, UBL Proteins Conference, Feb. 10-13, (2010).

Swords, R.T., et al., "The Novel, Investigational NEDD8-Activating Enzyme Inhibitor MLN4924 in Adult Patients with Acute Myeloid Leukemia (AML) or High-Grade Myelodysplastic Syndromes (MDS): A Phase 1 Study," Presented at the 52nd American Society for Hematology Meeting, 19 slides.

Swords, R.T., et al., "The Novel, Investigational NEDD8-Activating Enzyme Inhibitor MLN4924 in Adult Patients with Acute Myeloid Leukemia (AML) or High-Grade Myelodysplastic Syndromes (MDS): A Phase 1 Study," Oral Presentation No. 658,

(56) References Cited

OTHER PUBLICATIONS

Presented at the 52nd American Society of Hematology Annual Meeting, Dec. 4-7, Orlando, FL (2010).
Swords, R.T., et al., "Inhibition of NEDD8-activating enzyme: a novel approach for the treatment of acute myeloid leukemia," *Blood* 115 (18):3796-3800, The American Society of Hematology, United States (2010).
Swords, R.T., et al., "Personalized medicine for acute myelogenous leukemia—At the entrance gate," *American Journal of Hematology* 86:631-632, Wiley-Liss, Inc., United States (2011).
Takeda Pharmaceutical Company Limited, "More than Thirty Abstracts on VELCADE® and Leading Millennium Pipeline Compounds to be Presented in Oral Sessions at 53rd American Society of Hematology Annual Meeting," News Release of Nov. 8, 2011, accessed at https://web.archive.org/web/20130917130507/http://www.takeda.com/news/2011/20111109_3911.html, accessed on Mar. 29, 2017, 4 pages.
Thomas, M.P., et al., "MLN4924, an investigational NEDD8-Activating Enzyme inhibitor, induces differentiation in Acute Myelogenous Leukemia cell lines," *European Journal of Cancer* 48(Supplement 6):88, Abstract 286, Elsevier Inc., United States (2012).
Traore, T., et al. "Synergistic combination of MLN4924, an investigational small molecule inhibitor of NEDD8-activating enzyme (NAE), with azacitidine, a hypomethylating agent, in pre-clinical AML cancer models," *Haematologica* 97(s1):435, Abstract 1066, Ferrata-Storti Foundation, Italy (2012).
Traore, T., et al. "Synergistic combination of MLN4924, an investigational small molecule inhibitor of NEDD8-activating enzyme (NAE), with azacitidine, a hypomethylating agent, in pre-clinical AML cancer models," Poster Presented at 17th Congress of the European Hematology Association, Jun. 14-17, Amsterdam, The Netherlands (2012).
Wang, M., et al., "Targeting protein neddylation: a novel therapeutic strategy for the treatment of cancer," *Expert Opin. Ther. Targets* 15(3):253-264, Informa UK, Ltd., England (2011).
Wei, D., et al., "Radiosensitization of Human Pancreatic Cancer Cells by MLN4924, an Investigational NEDD8-Activating Enzyme Inhibitor," *Cancer Research* 72(1):282-293, American Association for Cancer Research, United States (2012).
Zhao, L., et al., "The NEDD8-activating enzyme inhibitor, MLN4924, cooperates with TRAIL to augment apoptosis through facilitating c-FLIP degradation in head and neck cancer cells," *Mol Cancer Ther* 10(12):2415-2425, American Association for Cancer Research, United States (2011).
Deangelo, D.J. et al., "MLN4924, a novel investigational inhibitor of NEDD8-activating enzyme, in adult patients with acute myeloid leukemia and myelodysplastic syndrome: Results from multiple dosing schedules in a phase 1 study," Abstract 1443, Presented at the 55th American Society for Hematology Meeting, Dec. 7-10, New Orleans, LA, United States (2013).
Extended European Search Report for EP Application No. 14797156.8, Munich, Germany, dated Apr. 12, 2017, 11 pages.
Erba, H.P. et al., "MLN4924, a novel, investigational NEDD8-activating enzyme inhibitor, in adult patients with acute myeloid leukemia or high-grade myelodysplastic syndromes: Results from a phase 1 study," Poster Presented at the 16th Congress of the European Hematology Association, Jun. 9-12, London, United Kingdom (2011).
Khalife, J.C., et al., "Targeting miR-155 via the NEDD8-Activating Enzyme Inhibitor MLN4924: a Novel Therapeutic Approach for Acute Myeloid Leukemia (AML)," Poster 3804 Presented at the 55th American Society of Hematology Meeting, Dec. 7-10, New Orleans, LA, United States (2013).
McDonald, A., et al., "Pharmacodynamic assays demonstrate NAE pathway inhibition following administration of MLN4924 in patients with acute myeloid leukemia," Poster Presented at the 17th Congress of the European Hematology Association, Jun. 14-17, Amsterdam, The Netherlands (2012).

Milhollen, M.A., et al., "Treatment Emergent Mutations in NAEβ Confer Resistance to the Investigational NEDD8-Activating Enzyme inhibitor MLN4924," Poster No. 1413 Presented at the 53rd American Society of Hematology Meeting, Dec. 10-13, San Diego, CA (2011).
Reidy, M., et al., "Effect of MLN4924 on TRAIL-Induced Apoptosis in Preclinical Models of Haematological Malignancies," Poster No. P-160, Presented at the 20th European Cell Death Organization Meeting, Sep. 14-17, Rome, Italy (2012).
Sen, S., et al., "Investigational NEDD8-Activating Enzyme (NAE) Inhibitor, MLN4924, Demonstrates Activity Against Primary AML Blast, Progenitor and Stem Cell Populations," Poster Presented at the 53rd American Society of Hematology Meeting, Dec. 10-13, San Diego, CA (2011).
Swords, R.T., et al., "MLN4924: A Inhibitor of the NEDD8 Activating Enzyme (NAE) has Potent Preclinical Activity Against Acute Myeloid Leukemia," Poster Presented at the 14th Congress of the European Hematology Association, Jun. 4-7, Berlin, Germany (2009).
Takeda, "C15010: Prior Therapies in Patients Who Achieved Response in Arm 2 (Pev/carb/pac)," Powerpoint slide, 1 page.
Thomas, M.P., et al., "MLN4924, an investigational NEDD8-activating enzyme inhibitor, induces differentiation in acute myelogenous leukemia cell lines," Poster Presented at the 24th EORTC—NCI—AACR Symposium on Molecular Targets and Cancer Therapeutics, Nov. 6-9, Dublin, Ireland (2012).
Harvey, R. D., "SIP Protocol Summary C15010.", Winship Clinical Trials., (2006), URL: https://oncore.emory edu/sip/SIPControlServlet.
Jazaeri, A., et al., "Overcoming platinum resistance in ovarian cancer using the novel compound MLN4924," Proceedings: AACR 104th Annual Meeting 73(8): Abstract 3380; Apr. 6-10, 2013; Washington, DC.
Lockhart, A. C., "A Phase 1B, Open-Label, Dose-Escalation, Multi-arm Study of MLN4924 Plus Docetaxel, Gemcitabine, or Combination of Carboplatin and Paclitaxel", Patients With Solid Tumors (C15010). Siteman Cancer Center, (2009), URL: http://www.siteman.wustl.edu/ProtDetail.aspx?ProtID=71868&mid=&id=1088, (Nov. 5, 2014).
Ma, C., et al., "A phase I and pharmacological study of sequences of the proteasome inhibitor, bortezomib (PS-341, Velcade), in combination with paclitaxel and carboplatin in patients with advanced malignancies," *Cancer Chemother Pharmacol* 59(2)207-15, Springer Media, Germany (2007).
Nawrocki et al., "Disrupting Protein NEDDylation with MLN4924 Is a Novel Strategy to Target Cisplatin Resistance in Ovarian Cancer.", *Clin Cancer Res* 19(13):3577-90, American Association for Cancer Research, United States (2013).
Pignata, S., et al., "A phase II study of weekly carboplatin and paclitaxel as first-line treatment of elderly patients with advanced ovarian cancer: A Multicentre Italian Trial in Ovarian Cancer (MITO-5) study," Critical Reviews in Oncology/ Hematology 66(3):229-236, Elsevier, Netherlands (2008).
Soto Parra, H., et al., "Three-week versus four-week schedule of cisplatin and gemcitabine: results of a randomized phase II study.", *Annals of Oncology* 13(7):1080-86, Oxford University Press, England (2002).
Wei et al., "Radiosensitization of Human Pancreatic Cancer Cells by MLN4924, an Investigational NEDD8-Activating Enzyme Inhibitor. ", *Cancer Res* 72(1):282-93, American Association for Cancer Research, United States (2011).
Huang T., et al., "Comparison of weekly versus every 3 weeks paclitaxel in the treatment of advanced solid tumors: a meta-analysis,", Cancer Treatment Reviews 38:613-617, Elsevier, Netherlands (2012).
Koeller, J.M., et al., "Phase 1 clinical trial and pharmokinetics of carboplatin (NSC 241240) by a single monthly 30 minute iinfusion," Cancer, 57(2), 222-5, American Association for Cancer Research, United States (1986).
Pauer L.R., et al., "Phase I study of oral CI-994 in comination with Carboplatin and Paclitaxel in the treatment of patients with advanced solid tumors," Cancer Investigation 22(6):886-896, Informa Healthcare, United States (2004).
Gao F., et al., "Neddylation of a breast cancer-associated protein recruits a class III histone deacetylase that represses NFkB-

(56) References Cited

OTHER PUBLICATIONS dependent transcription," Nature Cell Biology 8(10):1171-1177, Nature Publishing Group, England (2006).

* cited by examiner

ADMINISTRATION OF NEDD8-ACTIVATING ENZYME INHIBITOR AND CHEMOTHERAPEUTIC AGENTS

PRIORITY CLAIM

This application is a continuation of U.S. patent application Ser. No. 14/889,571 filed on Nov. 6, 2015, which is a national stage entry of PCT Application No. PCT/US2014/037888 filed on May 13, 2014, which claims priority to U.S. Provisional Application No. 61/822,994 filed on May 14, 2013, to U.S. Provisional Application No. 61/874,393 filed on Sep. 6, 2013 and to U.S. Provisional Application No. 61/891,943 filed on Oct. 17, 2013. The entire contents of each of the foregoing applications are incorporated herein by reference.

FIELD

This present disclosure relates to oncology and to methods for the treatment of cancer. In particular, the present disclosure provides methods for treatment of various solid tumors by administering a NEDD8-activating enzyme (NAE) inhibitor in combination with one or more chemotherapeutic agents.

BACKGROUND

Cancer is the second most common cause of death in the U.S. and accounts for one of every eight deaths worldwide. The National Cancer Institute estimates that approximately 13.7 million Americans with a history of cancer were alive on Jan. 1, 2012. Some of these individuals were cancer free, while others still had evidence of cancer and may have been undergoing treatment. About 1,660,290 new cancer cases are expected to be diagnosed in the US in 2013. In 2013, about 580,350 Americans are expected to die of cancer, almost 1,600 people per day. Although medical advances have improved cancer survival rates, there remains a continuing need for new and more effective treatment. Currently available treatments for solid tumors include neoadjuvant chemotherapy and/or radiation therapy and adjuvant chemotherapy and/or radiation therapy following surgical removal or resection. In addition, there are a number of newer targeted therapies that are also used in the treatment of various solid tumors.

Inhibition of NEDD8-activating enzyme (NAE) has been shown to induce cancer cell death and inhibit the growth of tumors in xenograft models. See, e.g., T. A. Soucy et al., *Nature*, 2009, 458, 732-737; T. A. Soucy et al., *Clin. Cancer Res.*, 2009, 15 (12), 3912-3916; and J. E. Brownell et al., *Mol. Cell.*, 2010, 37 (1), 102-111. Reports of Phase I clinical studies of an NAE inhibitor include R. T. Swords et al., *Blood*, 2010, 115, 3796-3800; J. S. Kauh et al., *J. Clin. Oncol.*, 2011, 29, abstract 3013; and S. Bhatia et al., *J. Clin. Oncol.*, 2011, 29, abstract 8529. Inhibitors of NAE are described in U.S. patent application Ser. No. 11/346,469 (Publ. No. 2006/0189636, U.S. Pat. No. 7,951,810), Ser. No. 11/700,614 (Publ. No. 2007/0191293) and Ser. No. 11/890,338 (Publ. No. 2008/0051404, U.S. Pat. No. 8,008,307).

New combinations of therapeutic agents that provide a beneficial effect in the treatment of solid tumors are desirable in order to prolong patient's lives while maintaining a high quality of life. Further, new combinations may provide an increased benefit as compared to each of the agents alone. This is especially true in the case where the solid tumors may be resistant or refractory to currently available therapeutic regimens.

SUMMARY

In one aspect, the present disclosure relates to methods of treating cancer comprising administering an NAE inhibitor and one or more chemotherapeutic agents in combination to a subject in need of such treatment.

In one aspect, the present disclosure relates to a kit comprising a medicament for use in treating cancer in a subject in need of such treatment. The kit comprises a medicament comprising an NAE inhibitor, and instructions for administering the NAE inhibitor and the one or more chemotherapeutic agents; or the kit comprises a medicament comprising the one or more chemotherapeutic agents, and instructions for administering the one or more chemotherapeutic agents and a NAE inhibitor. The kit can contain both a medicament comprising an NAE inhibitor and a medicament comprising one or more chemotherapeutic agents, and instructions for administering the NAE inhibitor and the one or more chemotherapeutic agents.

In one aspect, the present disclosure relates to a medicament for use in treating cancer in a subject in need of such treatment. The medicament comprises an NAE inhibitor and one or more chemotherapeutic agents.

DESCRIPTION

Definitions and Abbreviations

Figure 1:
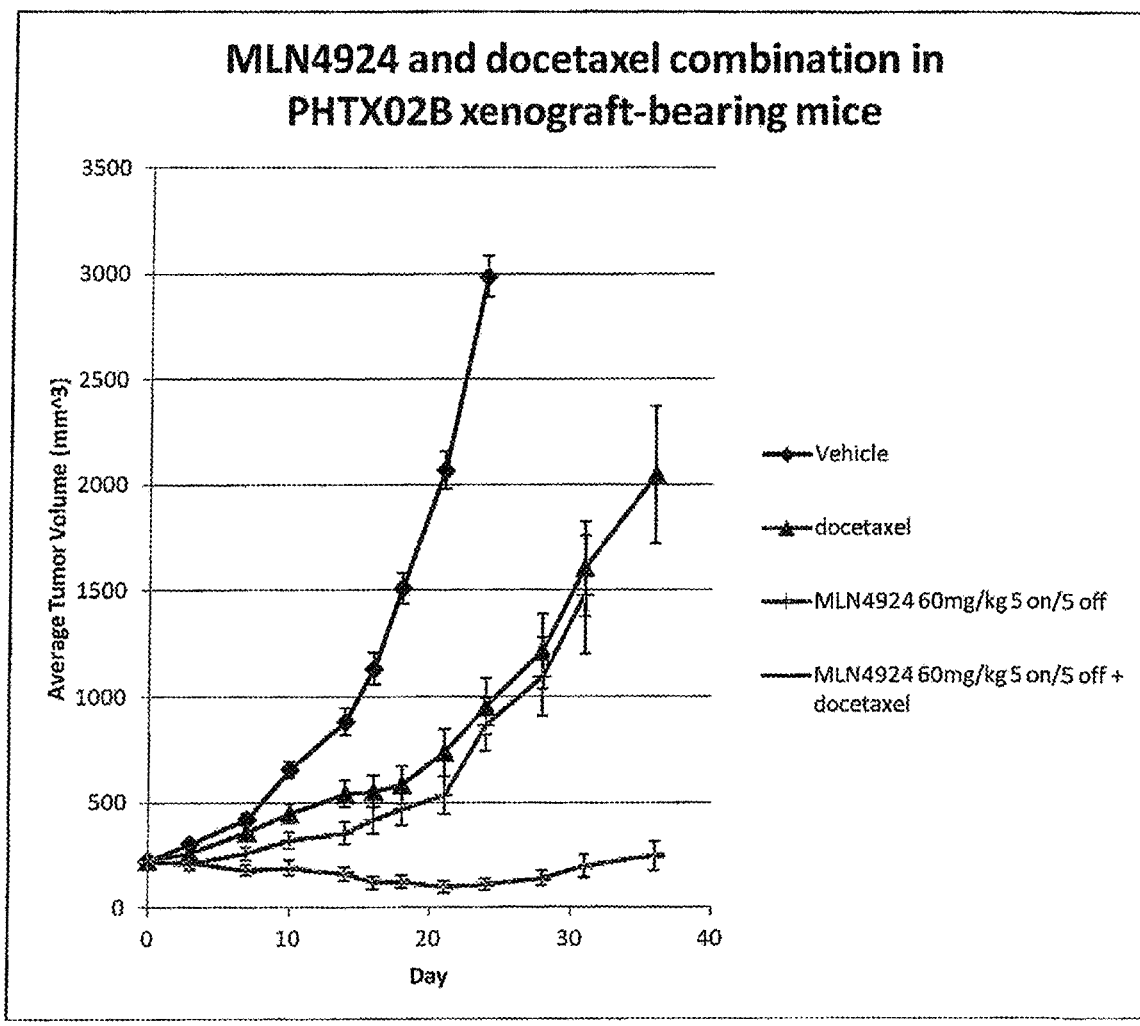
FIG. 1 shows a plot of tumor volume as a function of time in a PHTX02B xenograft model following administration of MLN4924 and docetaxel to mice.

AUC area under the plasma concentration versus time curve
BSA body surface area
CR complete response
MTD maximum tolerated dose
NAE Nedd8-activating enzyme
Nedd8 neural precursor cell expressed, developmentally down-regulated 8
PR partial response
QD once daily
SCLC small cell lung cancer As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer" includes solid tumors and hematological tumors. The term "cancer" encompasses diseases of skin, tissues, organs, bone, cartilage, blood, and vessels. The term "cancer" further encompasses primary and metastatic cancers.

As used herein, "clinically effective amount" means an amount of a therapeutic substance that is sufficient upon appropriate administration to a patient (a) to cause a detectable decrease in the severity of the disorder or disease state being treated; (b) to ameliorate or alleviate the patient's symptoms of the disease or disorder; or (c) to slow or prevent advancement of, or otherwise stabilize or prolong stabilization of, the disorder or disease state being treated (e.g., prevent additional tumor growth of a cancer).

When more than one therapeutic substance is being administered, the "clinically effective total amount" means that the sum of the individual amounts of each therapeutic substance meets the definition of "clinically effective amount" even if the individual amounts of any number of the individual therapeutic substances would not. For example, if 10 mg of A were not a clinically effective amount, and 20 mg of B were not a clinically effective amount, but the administration of 10 mg A+20 mg B resulted in at least one of the results enumerated for the definition of "clinically effective amount", then the sum of 10 mg A+20 mg B would be considered a "clinically effective total amount".

In any form or composition, the administered dose(s) or the clinically effective (total) amount can be expressed as amount(s) of therapeutic substance(s) per patient BSA, e.g., as mg/m$^2$.

As used herein, "patient" means a human being diagnosed with, exhibiting symptoms of or otherwise believed to be afflicted with a disease, disorder or condition.

As used herein, "body surface area" (BSA) is calculated using a standard nomogram, e.g., $$BSA(m^2) = \sqrt{\frac{Ht(cm) \times Wt(kg)}{3600}} \text{ or } BSA = \sqrt{\frac{Ht(in) \times Wt(lb)}{3131}}$$

As used herein, dosing for carboplatin is based upon an estimate of the GFR (glomerular filtration rate) and the desired level of drug exposure, according to the area under the curve of concentration×time (AUC, mg/mL×min), rather than the more common dosing calculation based upon the body surface area (mg/m$^2$). For a desired target AUC (which typically varies between 5 and 7 mg/mL×min) and the estimated GFR, the dose of carboplatin is then calculated by use of the Calvert formula:

Total carboplatin dose, mg=Target AUC×(estimated creatinine clearance+25).

Because of potential changes in weight or renal function, this calculation should be repeated prior to each administered course of carboplatin.

The estimation of the GFR is based upon a calculation of creatinine clearance according to the Cockcroft-Gault Equation (Cockcroft D W, Gault M H. Prediction of creatinine clearance from serum creatinine. Nephron. 1976; 16(1):31-41):

For Males:

Creatinine Clearance=(140-age [years]×weight [kg])/ 72×(serum creatinine [mg/dL])

For Females:

Creatinine Clearance=0.85(140-age [years]×weight [kg])/72×(serum creatinine [mg/dL]).

As used herein, the illustrative terms "include", "such as", "for example" and the like (and variations thereof, e.g., "includes" and "including", "examples"), unless otherwise specified, are intended to be non-limiting. That is, unless explicitly stated otherwise, such terms are intended to imply "but not limited to", e.g., "including" means including but not limited to.

DETAILED DESCRIPTION

In some embodiments, the present disclosure relates to a method of treating solid tumors in a patient by administering to a patient a combination of MLN4924 and one or more chemotherapeutic agents, wherein the chemotherapeutic agent is: (i) a taxane; (ii) a platin; or (iii) gemcitabine.

The compound ((1S,2S,4R)-4-(4-((1S)-2,3-dihydro-1H-inden-1-ylamino)-7H-pyrrolo[2,3-d]-pyrimidin-7-yl)-2-hydroxycyclopentyl)methyl sulfamate:

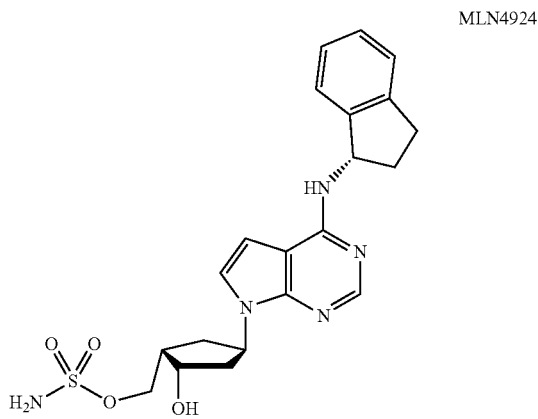

MLN4924 also known as MLN4924, is an inhibitor of NEDD8-activating enzyme (NAE). See. e.g., T. A. Soucy et al., *Nature*, 2009, 458, 732-737; T. A. Soucy et al., *Clin. Cancer Res.*, 2009, 15 (12), 3912-3916; and J. E. Brownell et al., *Mol. Cell.*, 2010, 37 (1), 102-111, each of which is hereby incorporated by reference herein in its entirety. MLN4924, pharmaceutical compositions of MLN4924, processes for its synthesis, and polymorphic forms have been described previously. See, e.g., U.S. patent application Ser. No. 11/700,614 (Publ. No. 2007/0191293), Ser. No. 12/221,399 (Publ. No. 2009/0036678) and Ser. No. 12/779,331 (Publ. No. 2011/0021544), each of which is hereby incorporated by reference herein in its entirety. If there is any discrepancy between any of these documents and the present specification, the present specification controls.

In another aspect, the present disclosure relates to the use of MLN4924 or a pharmaceutically acceptable salt in combination with one or more chemotherapeutic agents, wherein the chemotherapeutic agent is: (i) a taxane; (ii) a platin; or (iii) gemcitabine for the treatment of solid tumors.

In another aspect, the present disclosure relates to the use of MLN4924 or a pharmaceutically acceptable salt in combination with one or more chemotherapeutic agents, wherein the chemotherapeutic agent is: (i) a taxane; (ii) a platin; or (iii) gemcitabine in the manufacture of a medicament for use in treating solid tumors.

In another aspect, the present disclosure relates to the use of MLN4924 or a pharmaceutically acceptable salt in the manufacture of a medicament for treating solid tumors, wherein the MLN4924 or a pharmaceutically acceptable salt thereof is administered with one or more chemotherapeutic agents, wherein the chemotherapeutic agent is: (i) a taxane; (ii) a platin; or (iii) gemcitabine.

In another aspect, the present disclosure relates to a kit for treating solid tumors comprising at least one medicament comprising at least one dose of MLN4924 or a pharmaceutically acceptable salt thereof, and at least one medicament comprising at least one dose of one or more of: (i) a platin; (ii) a taxane; or (iii) gemcitabine or a pharmaceutically acceptable salt thereof, said kit for treating solid tumors further comprising dosing instructions for administering the medicaments for treatment of the subject in recognized need thereof.

MLN4924 or a pharmaceutically acceptable salt thereof can be administered in combination with the one or more chemotherapeutic agents in a single dosage form or as a separate dosage forms. In one embodiment, when administered as a separate dosage form, the one or more chemotherapeutic agents can be administered prior to, at the same time as, or following administration of MLN4924. In some embodiments, when administered as a separate dosage form, one or more doses of MLN4924 or a pharmaceutically acceptable salt thereof, may be administered prior to the one or more chemotherapeutic agents. In some embodiments, the one or more therapeutic agents is administered prior to the administration of MLN4924 or a pharmaceutically acceptable salt thereof. As used herein, the administration in "combination" of MLN4924 and a chemotherapeutic agent refers not only to simultaneous or sequential administration of the two agents, but also to the administration of both compounds during a single treatment cycle, as understood by one skilled in the art. When MLN4924 or a pharmaceutically acceptable salt thereof is administered in combination with the one or more chemotherapeutic agents a clinically effective total amount is administered.

In some embodiments, MLN4924 or a pharmaceutically acceptable salt is administered intravenously (IV). In some embodiments, the one or more chemotherapeutic agents is administered intravenously (IV).

In some embodiments, the one or more chemotherapeutic agent is one chemotherapeutic agent. In some embodiments, the one or more chemotherapeutic agents is two chemotherapeutic agents. In some embodiments, the one or more chemotherapeutic agents is three chemotherapeutic agents.

In some embodiments, the chemotherapeutic agent is a platinum containing compound ("platin"). Platinum containing compounds include agents such as cisplatin, carboplatin, oxaliplatin, satraplatin, picoplatin, nedaplatin and triplatin. Platinum containing chemotherapeutic agents cause cross-linking of DNA as monoadduct, interstrand crosslinks, intrastrand crosslinks or DNA protein crosslinks. The resulting crosslinking inhibits DNA repair and/or DNA synthesis in cancer cells. These agents are sometimes described as being alkylating-like agents despite the fact that they do not have an alkyl group. Cisplatin was the first platinum containing compound to be discovered and was first approved by the U.S. Food and Drug Administration in 1978. Carboplatin was introduced in the 1980s and has been demonstrated to have lower side-effects than cisplatin in ovarian cancer and lung cancer (Hartmann and Lipp, *Exper. Opin. Pharmacother.* 2003, 4(6) 889-901).

In some embodiments, the platin is cisplatin, carboplatin, oxaliplatin, satraplatin, picoplatin, nedaplatin or triplatin. In some embodiments, the platin is nedaplatin, cisplatin, carboplatin or oxaliplatin. In some embodiments, the platin is cisplatin, carboplatin or oxaliplatin. In some embodiments, the platin is cisplatin. In some embodiments, the platin is carboplatin. In some embodiments, the platin is cisplatin or carboplatin.

In some embodiments, the chemotherapeutic agent is gemcitabine or a pharmaceutically acceptable salt. Gemcitabine is a nucleoside analog that works by disrupting DNA replication. Gemcitabine is approved for treatment by the U.S. Food and Drug Administration for the treatment of several cancers including pancreatic cancer, non-small cell lung cancer and breast cancer. Gemcitabine can be in the form of a pharmaceutically acceptable salt, such as an acid addition salt. In some embodiments, the acid addition salt of gemcitabine is gemcitabine hydrochloride. One form of gemcitabine is currently marketed as GEMZAR® (Eli Lilly and Company).

In some embodiments, the chemotherapeutic agent is a taxane. Taxanes are diterpenes produced by the plants of the genus Taxus (yew trees). Taxanes were first discovered and isolated from this natural source but are mostly now produced by synthetic or semi-synthetic methods. The principle mechanism by which taxanes exert their effect is the disruption of microtubule function during cell division, thereby preventing effective growth and division of cancer cells.

Taxane agents include paclitaxel and docetaxel. Paclitaxel was originally isolated from the bark of the Pacific yew tree and was subsequently produced in a semi-synthetic manner. Paclitaxel was first approved by the U.S. Food and Drug Administration in 1992. Docetaxel is also derived semi-synthetically from the needles of the yew tree. Docetaxel is approved by the U.S. Food and Drug Administration for the treatment of advanced breast, lung, and ovarian cancer. An alternative formulation of paclitaxel where the paclitaxel is bound to albumin nano-particles, known as nab-paclitaxel [marketed as Abraxane (Celgene Corporation)] is also approved by the U.S. Food and Drug Administration for certain types of metastatic breast cancer. In some embodiments, the taxane is paclitaxel, docetaxel or nab-paclitaxel. In some embodiments, the taxane is paclitaxel or docetaxel. In some embodiments, the taxane is paclitaxel. In some embodiments, the taxane is docetaxel.

In some embodiments, the cancer is a solid tumor. In some embodiments, the solid tumor is breast cancer, colon cancer, lung cancer, pancreatic cancer, bladder cancer, esophageal cancer, or head and neck cancer. In some embodiments, the solid tumor is breast cancer, colon cancer, lung cancer, pancreatic cancer, bladder cancer, esophageal cancer, head and neck cancer or cholangiocarcinoma. In some embodiments, the solid tumor is breast cancer, colon cancer, lung cancer or pancreatic cancer. In some embodiment, the solid tumor is colon cancer, lung cancer or pancreatic cancer. In some embodiments, the solid tumor is lung cancer or pancreatic cancer. In some embodiments, the solid tumor is lung cancer, head and neck cancer or cholangiocarcinoma. In some embodiments, the solid tumor is lung cancer or head and neck cancer.

In some embodiments, the solid tumor is lung cancer. Lung cancer includes different sub-types such as small cell lung cancer (SCLC); non-small cell lung cancer (NSCLC) including squamous NSCLC; bronchioloalveolar carcinoma (BAC); and adenocarcinoma. In some embodiments, the solid tumor is small cell lung cancer. In some embodiments, the solid tumor is non-small cell lung cancer. In some embodiments, the solid tumor is squamous non-small cell lung cancer.

In some embodiments, the solid tumor is breast cancer. Breast cancer includes different sub-types such as luminal A, luminal B, triple-negative (basal-like) and HER-2 type. In some embodiments, the solid tumor is triple-negative breast cancer.

In some embodiments, the solid tumor is esophageal cancer. Esophageal cancer includes sub-types of adenocarcinoma and squamous. In some embodiments, the solid tumor is squamous esophageal cancer.

In some embodiments, the solid tumor is head and neck cancer. Head and neck cancer are those that arise in the head and neck region and the cancer may be found in areas such as nasal cavities, sinuses, lips, mouth, salivary glands, pharynx or larynx. 90% of head and neck cancers are squamous cell carcinomas (SCCHN), which originate from the mucosal lining (epithelium) of these regions. In some embodiments, the solid tumor is squamous head and neck cancer.

In some embodiments, the solid tumor is colon cancer. In some embodiments, the solid tumor is pancreatic cancer. In some embodiments, the solid tumor is biliary tract cancers which include cholangiocarcinoma, pancreatic cancer, gallbladder cancer, and cancer of the ampulla of Vater. In some embodiments, the solid tumor is cholangiocarcinoma.

In some embodiments, the solid tumor is bladder cancer. Bladder cancer includes both non-invasive and invasive sub-types. In some embodiments, the solid tumor is invasive bladder cancer.

In some embodiments, the method of treatment further comprises the use of radiotherapy. The radiotherapy may be administered prior to the administration of the combination or after the administration of the combination.

In some embodiments, MLN4924 or a pharmaceutically acceptable salt thereof is administered on each of days 1, 3, and 5 of a 21 day schedule. In some embodiments, the amount of MLN4924 or a pharmaceutically acceptable salt thereof that is administered on each of days 1, 3, and 5 of a 21 day schedule is less than or equal to 50 mg/m$^2$. In some embodiments, the amount of MLN4924 or a pharmaceutically acceptable salt thereof that is administered on each of days 1, 3, and 5 of a 21 day schedule is 50 mg/m$^2$. In some embodiments, the amount of MLN4924 or a pharmaceutically acceptable salt thereof that is administered on each of days 1, 3, and 5 of a 21 day schedule is 37 mg/m$^2$. In some embodiments, the amount of MLN4924 or a pharmaceutically acceptable salt thereof that is administered on each of days 1, 3, and 5 of a 21 day schedule is 25 mg/m$^2$. In some embodiments, the amount of MLN4924 or a pharmaceutically acceptable salt thereof that is administered on each of days 1, 3, and 5 of a 21 day schedule is 15 mg/m$^2$. In some embodiments, the amount of MLN4924 or a pharmaceutically acceptable salt thereof that is administered on each of days 1, 3, and 5 of a 21 day schedule is 20 mg/m$^2$. In some embodiments, the amount of MLN4924 or a pharmaceutically acceptable salt thereof that is administered on each of days 1, 3, and 5 of a 21 day schedule is about 10 mg/m$^2$ to about 30 mg/m$^2$.

In some embodiments, MLN4924 or a pharmaceutically acceptable salt thereof is administered on each of days 1, 8, and 15 of a 28 day schedule. In some embodiments, the amount of MLN4924 or a pharmaceutically acceptable salt thereof that is administered on each of days 1, 8, and 15 of a 28 day schedule is less than or equal to 100 mg/m$^2$. In some embodiments, the amount of MLN4924 or a pharmaceutically acceptable salt thereof that is administered on each of days 1, 8, and 15 of a 28 day schedule is 100 mg/m$^2$. In some embodiments, the amount of MLN4924 or a pharmaceutically acceptable salt thereof that is administered on each of days 1, 8, and 15 of a 28 day schedule is 75 mg/m$^2$. In some embodiments, the amount of MLN4924 or a pharmaceutically acceptable salt thereof that is administered on each of days 1, 8, and 15 of a 28 day schedule is 50 mg/m$^2$. In some embodiments, the amount of MLN4924 or a pharmaceutically acceptable salt thereof that is administered on each of days 1, 8, and 15 of a 28 day schedule is 25 mg/m$^2$. In some embodiments, the amount of MLN4924 or a pharmaceutically acceptable salt thereof that is administered on each of days 1, 8, and 15 of a 28 day schedule is 20 mg/m$^2$. In some embodiments, the amount of MLN4924 or a pharmaceutically acceptable salt thereof that is administered on each of days 1, 8, and 15 of a 28 day schedule is 15 mg/m$^2$. In some embodiments, the amount of MLN4924 or a pharmaceutically acceptable salt thereof that is administered on each of days 1, 8, and 15 of a 28 day schedule is about 15 mg/m$^2$ to about 40 mg/m$^2$.

In some embodiments, MLN4924 or a pharmaceutically acceptable salt thereof is administered on day 1 of a 21 day schedule. In some embodiments, the amount of MLN4924 or a pharmaceutically acceptable salt thereof that is administered on day 1 of a 21 day schedule is less than or equal to 50 mg/m$^2$. In some embodiments, the amount of MLN4924 or a pharmaceutically acceptable salt thereof that is administered on day 1 of a 21 day schedule is less than or equal to 25 mg/m$^2$. In some embodiments, the amount of MLN4924 or a pharmaceutically acceptable salt thereof that is administered on day 1 of a 21 day schedule is 20 mg/m$^2$. In some embodiments, the amount of MLN4924 or a pharmaceutically acceptable salt thereof that is administered on day 1 of a 21 day schedule is less than or equal to 15 mg/m$^2$. In some embodiments, MLN4924 or a pharmaceutically acceptable salt thereof is administered on day 1 of a 28 day schedule. In some embodiments, the amount of MLN4924 or a pharmaceutically acceptable salt thereof that is administered on day 1 of a 28 day schedule is less than or equal to 100 mg/m$^2$.

In some embodiments, the one or more chemotherapeutic agents is administered on day 1 of a 21 day schedule. In some embodiments, a taxane is administered on day 1 of a 21 day schedule. In some embodiments, docetaxel is administered on day 1 of a 21 day schedule. In some embodiments, the amount of docetaxel that is administered on day 1 of a 21 day schedule is 75 mg/m$^2$. In some embodiments, the amount of docetaxel that is administered on day 1 of a 21 day schedule is about 50 mg/m$^2$ to about 100 mg/m$^2$. In some embodiments, paclitaxel is administered of day 1 of a 21 day schedule. In some embodiments, the amount of paclitaxel that is administered on day 1 of a 21 day schedule is 200 mg/m$^2$. In some embodiments, the amount of paclitaxel that is administered on day 1 of a 21 day schedule is 175 mg/m$^2$. In some embodiments, the amount of paclitaxel that is administered on day 1 of a 21 day schedule is 135 mg/m$^2$. In some embodiments, the amount of paclitaxel that is administered on day 1 of a 21 day schedule is about 135 mg/m$^2$ to about 200 mg/m$^2$.

In some embodiments, a platin is administered on day 1 of a 21 day schedule. In some embodiments, carboplatin is administered on day 1 of a 21 day schedule. In some embodiments, the amount of carboplatin that is administered on day 1 of a 21 day schedule is AUC 6 (calculated as per the Calvert calculation above). In some embodiments, the amount of carboplatin that is administered on day 1 of 21 day schedule is AUC 5.

In some embodiments, cisplatin is administered on day 1 of a 21 day schedule. In some embodiments, the total amount of cisplatin administered is less than or equal to 100 mg/m$^2$. In some embodiments, the amount of cisplatin administered on day 1 of a 21 day schedule is about 75 mg/m$^2$ to about 100 mg/m$^2$. In some embodiments, the amount of cisplatin administered on day 1 of a 21 day schedule is about 50 mg/m² to about 70 mg/m². In some embodiments, cisplatin is administered on each of days 1, 2, and 3 of a 21 day schedule. In some embodiments, cisplatin is administered on each of days 1, 3, and 5 of a 21 day schedule. In some embodiments, the total amount of cisplatin administered is less than or equal to 100 mg/m². In some embodiments, the amount of cisplatin that is administered on each of days 1, 2, and 3 of a 21 day schedule is 25 mg/m. In some embodiments, the amount of cisplatin that is administered on each of days 1, 3, and 5 of a 21 day schedule is 25 mg/m².

In some embodiments, the one or more chemotherapeutic agents is administered on each of days 1, 8, and 15 of a 28 day schedule. In some embodiments, gemicitabine is administered on each of days 1, 8, and 15 of a 28 day schedule. In some embodiments, the amount of gemicitabine that is administered on each of days 1, 8, and 15 of a 28 day schedule is 1000 mg/m². In some embodiments, the amount of gemicitabine that is administered on each of days 1, 8, and 15 of a 28 day schedule is 800 mg/m².

In some embodiments, MLN4924 or a pharmaceutically acceptable salt thereof is administered on each of days 1, 3, and 5 of a 21 day schedule, and the one or more chemotherapeutic agent is administered on day 1 of a 21 day schedule. In some embodiments, MLN4924 or a pharmaceutically acceptable salt thereof is administered on each of days 1, 3, and 5 of a 21 day schedule, and one chemotherapeutic agent is administered on day 1 of a 21 day schedule. In some embodiments, MLN4924 or a pharmaceutically acceptable salt thereof is administered on each of days 1, 3, and 5 of a 21 day schedule, and two chemotherapeutic agents are administered on day 1 of a 21 day schedule.

In some embodiments, MLN4924 or a pharmaceutically acceptable salt thereof is administered on each of days 1, 3, and 5 of a 21 day schedule, and a taxane is administered on day 1 of a 21 day schedule. In some embodiments, MLN4924 or a pharmaceutically acceptable salt thereof is administered on each of days 1, 3, and 5 of a 21 day schedule, and docetaxel is administered on day 1 of a 21 day schedule. In some embodiments, MLN4924 or a pharmaceutically acceptable salt thereof is administered on each of days 1, 3, and 5 of a 21 day schedule, and paclitaxel is administered on day 1 of a 21 day schedule.

In some embodiments, MLN4924 or a pharmaceutically acceptable salt thereof is administered on each of days 1, 3, and 5 of a 21 day schedule, and a platin is administered on day 1 of a 21 day schedule. In some embodiments, MLN4924 or a pharmaceutically acceptable salt thereof is administered on each of days 1, 3, and 5 of a 21 day schedule, and carboplatin is administered on day 1 of a 21 day schedule. In some embodiments, MLN4924 or a pharmaceutically acceptable salt thereof is administered on each of days 1, 3, and 5 of a 21 day schedule, and oxaliplatin is administered on day 1 of a 21 day schedule.

In some embodiments, MLN4924 or a pharmaceutically acceptable salt thereof is administered on each of days 1, 3, and 5 of a 21 day schedule, and cisplatin is administered on day 1 of a 21 day schedule. In some embodiments, MLN4924 or a pharmaceutically acceptable salt thereof is administered on each of days 1, 3, and 5 of a 21 day schedule, and cisplatin is administered on each of days 1, 2, and 3 of a 21 day schedule. In some embodiments, MLN4924 or a pharmaceutically acceptable salt thereof is administered on each of days 1, 3, and 5 of a 21 day schedule, and cisplatin is administered on each of days 1, 3, and 5 of a 21 day schedule.

In some embodiments, MLN4924 or a pharmaceutically acceptable salt thereof is administered on each of days 1, 3, and 5 of a 21 day schedule, and a taxane and a platin are administered on day 1 of a 21 day schedule. In some embodiments, MLN4924 or a pharmaceutically acceptable salt thereof is administered on each of days 1, 3, and 5 of a 21 day schedule, and paclitaxel and carboplatin are administered on day 1 of a 21 day schedule. In some embodiments, MLN4924 or a pharmaceutically acceptable salt thereof is administered on each of days 1, 3, and 5 of a 21 day schedule, and paclitaxel and cisplatin are administered on day 1 of a 21 day schedule. In some embodiments, MLN4924 or a pharmaceutically acceptable salt thereof is administered on each of days 1, 3, and 5 of a 21 day schedule, and docetaxel and carboplatin are administered on day 1 of a 21 day schedule. In some embodiments, MLN4924 or a pharmaceutically acceptable salt thereof is administered on each of days 1, 3, and 5 of a 21 day schedule, and docetaxel and cisplatin are administered on day 1 of a 21 day schedule.

In some embodiments, MLN4924 or a pharmaceutically acceptable salt thereof is administered on each of days 1, 8, and 15 of a 28 day schedule and the one or more chemotherapeutic agent is administered on each of days 1, 8, and 15 of a 28 day schedule. In some embodiments, MLN4924 or a pharmaceutically acceptable salt thereof is administered on each of days 1, 8, and 15 of a 28 day schedule, and one chemotherapeutic agent is administered on each of days 1, 8, and 15 of a 28 day schedule. In some embodiments, MLN4924 or a pharmaceutically acceptable salt thereof is administered on each of days 1, 8, and 15 of a 28 day schedule, and gemcitabine is administered on each of days 1, 8, and 15 of a 28 day schedule.

In some embodiments, wherein the solid tumor is colon cancer, the method comprises administering to a patient in need of such treatment a combination of MLN4924 or a pharmaceutically acceptable salt thereof and a taxane. In some embodiments, wherein the solid tumor is colon cancer, the method comprises administering to a patient in need of such treatment a combination of MLN4924 or a pharmaceutically acceptable salt thereof and docetaxel. In some embodiments, wherein the solid tumor is colon cancer, the method comprises administering to a patient in need of such treatment a combination of MLN4924 or a pharmaceutically acceptable salt thereof and paclitaxel.

In some embodiments, wherein the solid tumor is colon cancer, the method comprises administering to a patient in need of such treatment a combination of MLN4924 or a pharmaceutically acceptable salt thereof and a platin. In some embodiments, wherein the solid tumor is colon cancer, the method comprises administering to a patient in need of such treatment a combination of MLN4924 or a pharmaceutically acceptable salt thereof and oxaliplatin.

In some embodiments, wherein the solid tumor is breast cancer, the method comprises administering to a patient in need of such treatment a combination of MLN4924 or a pharmaceutically acceptable salt thereof and a taxane. In some embodiments, wherein the solid tumor is breast cancer, the method comprises administering to a patient in need of such treatment a combination of MLN4924 or a pharmaceutically acceptable salt thereof and docetaxel. In some embodiments, wherein the solid tumor is breast cancer, the method comprises administering to a patient in need of such treatment a combination of MLN4924 or a pharmaceutically acceptable salt thereof and paclitaxel.

In some embodiments, wherein the solid tumor is lung cancer, the method comprises administering to a patient in need of such treatment a combination of MLN4924 or a pharmaceutically acceptable salt thereof, and a platin. In some embodiments, wherein the solid tumor is lung cancer, the method comprises administering to a patient in need of such treatment a combination of MLN4924 or a pharmaceutically acceptable salt thereof, and carboplatin. In some embodiments, wherein the solid tumor is lung cancer, the method comprises administering to a patient in need of such treatment a combination of MLN4924 or a pharmaceutically acceptable salt thereof, and cisplatin. In some embodiments, wherein the solid tumor is lung cancer, the method comprises administering to a patient in need of such treatment a combination of MLN4924 or a pharmaceutically acceptable salt thereof, and nedaplatin. In some embodiments, wherein the solid tumor is small cell lung cancer, the method comprises administering to a patient in need of such treatment a combination of MLN4924 or a pharmaceutically acceptable salt thereof, and carboplatin. In some embodiments, wherein the solid tumor is small cell lung cancer, the method comprises administering to a patient in need of such treatment a combination of MLN4924 or a pharmaceutically acceptable salt thereof, and cisplatin. In some embodiments, wherein the solid tumor is small cell lung cancer, the method comprises administering to a patient in need of such treatment a combination of MLN4924 or a pharmaceutically acceptable salt thereof, and nedaplatin. In some embodiments, wherein the solid tumor is non-small cell lung cancer, the method comprises administering to a patient in need of such treatment a combination of MLN4924 or a pharmaceutically acceptable salt thereof, and carboplatin. In some embodiments, wherein the solid tumor is non-small cell lung cancer, the method comprises administering to a patient in need of such treatment a combination of MLN4924 or a pharmaceutically acceptable salt thereof, and cisplatin. In some embodiments, wherein the solid tumor is non-small cell lung cancer, the method comprises administering to a patient in need of such treatment a combination of MLN4924 or a pharmaceutically acceptable salt thereof, and nedaplatin. In some embodiments, wherein the solid tumor is squamous non-small cell lung cancer, the method comprises administering to a patient in need of such treatment a combination of MLN4924 or a pharmaceutically acceptable salt thereof, and carboplatin. In some embodiments, wherein the solid tumor is squamous non-small cell lung cancer, the method comprises administering to a patient in need of such treatment a combination of MLN4924 or a pharmaceutically acceptable salt thereof, and cisplatin. In some embodiments, wherein the solid tumor is squamous non-small cell lung cancer, the method comprises administering to a patient in need of such treatment a combination of MLN4924 or a pharmaceutically acceptable salt thereof, and nedaplatin.

In some embodiments, wherein the solid tumor is lung cancer, the method comprises administering to a patient in need of such treatment a combination of MLN4924 or a pharmaceutically acceptable salt thereof, a taxane and a platin. In some embodiments, wherein the solid tumor is lung cancer, the method comprises administering to a patient in need of such treatment a combination of MLN4924 or a pharmaceutically acceptable salt thereof, paclitaxel and carboplatin. In some embodiments, wherein the solid tumor is small cell lung cancer, the method comprises administering to a patient in need of such treatment a combination of MLN4924 or a pharmaceutically acceptable salt thereof, paclitaxel and carboplatin. In some embodiments, wherein the solid tumor is non-small cell lung cancer, the method comprises administering to a patient in need of such treatment a combination of MLN4924 or a pharmaceutically acceptable salt thereof, paclitaxel and carboplatin. In some embodiments, wherein the solid tumor is squamous non-small cell lung cancer, the method comprises administering to a patient in need of such treatment a combination of MLN4924 or a pharmaceutically acceptable salt thereof, paclitaxel and carboplatin.

In some embodiments, wherein the solid tumor is lung cancer, the method comprises administering to a patient in need of such treatment a combination of MLN4924 or a pharmaceutically acceptable salt thereof, gemcitabine and a platin. In some embodiments, wherein the solid tumor is lung cancer, the method comprises administering to a patient in need of such treatment a combination of MLN4924 or a pharmaceutically acceptable salt thereof, gemcitabine and carboplatin. In some embodiments, wherein the solid tumor is small cell lung cancer, the method comprises administering to a patient in need of such treatment a combination of MLN4924 or a pharmaceutically acceptable salt thereof, gemcitabine and carboplatin. In some embodiments, wherein the solid tumor is non-small cell lung cancer, the method comprises administering to a patient in need of such treatment a combination of MLN4924 or a pharmaceutically acceptable salt thereof, gemcitabine and carboplatin. In some embodiments, wherein the solid tumor is squamous non-small cell lung cancer, the method comprises administering to a patient in need of such treatment a combination of MLN4924 or a pharmaceutically acceptable salt thereof, gemcitabine and carboplatin. In some embodiments, wherein the solid tumor is lung cancer, the method comprises administering to a patient in need of such treatment a combination of MLN4924 or a pharmaceutically acceptable salt thereof, gemcitabine and cisplatin. In some embodiments, wherein the solid tumor is small cell lung cancer, the method comprises administering to a patient in need of such treatment a combination of MLN4924 or a pharmaceutically acceptable salt thereof, gemcitabine and cisplatin. In some embodiments, wherein the solid tumor is non-small cell lung cancer, the method comprises administering to a patient in need of such treatment a combination of MLN4924 or a pharmaceutically acceptable salt thereof, gemcitabine and cisplatin. In some embodiments, wherein the solid tumor is squamous non-small cell lung cancer, the method comprises administering to a patient in need of such treatment a combination of MLN4924 or a pharmaceutically acceptable salt thereof, gemcitabine and cisplatin.

In some embodiments, wherein the solid tumor is lung cancer, the method comprises administering to a patient in need of such treatment a combination of MLN4924 or a pharmaceutically acceptable salt thereof and a taxane. In some embodiments, wherein the solid tumor is lung cancer, the method comprises administering to a patient in need of such treatment a combination of MLN4924 or a pharmaceutically acceptable salt thereof and docetaxel. In some embodiments, wherein the solid tumor is small cell lung cancer, the method comprises administering to a patient in need of such treatment a combination of MLN4924 or a pharmaceutically acceptable salt thereof and docetaxel. In some embodiments, wherein the solid tumor is non-small cell lung cancer, the method comprises administering to a patient in need of such treatment a combination of MLN4924 or a pharmaceutically acceptable salt thereof, and docetaxel. In some embodiments, wherein the solid tumor is squamous non-small cell lung cancer, the method comprises administering to a patient in need of such treatment a combination of MLN4924 or a pharmaceutically acceptable salt thereof, and docetaxel.

In some embodiments, wherein the solid tumor is pancreatic cancer, the method comprises administering to a patient in need of such treatment a combination of MLN4924 or a pharmaceutically acceptable salt thereof and gemcitabine.

In some embodiments, wherein the solid tumor is invasive bladder cancer, the method comprises administering to a patient in need of such treatment a combination of MLN4924 or a pharmaceutically acceptable salt thereof, gemcitabine and cisplatin. In some embodiments, wherein the solid tumor is invasive bladder cancer, the method comprises administering to a patient in need of such treatment a combination of MLN4924 or a pharmaceutically acceptable salt thereof, gemcitabine and carboplatin.

In some embodiments, wherein the solid tumor is squamous esophageal cancer, the method comprises administering to a patient in need of such treatment a combination of MLN4924 or a pharmaceutically acceptable salt thereof and a taxane. In some embodiments, wherein the solid tumor is squamous esophageal cancer, the method comprises administering to a patient in need of such treatment a combination of MLN4924 or a pharmaceutically acceptable salt thereof and docetaxel.

In some embodiments, wherein the solid tumor is head and neck cancer, the method comprises administering to a patient in need of such treatment a combination of MLN4924 or a pharmaceutically acceptable salt thereof and a taxane. In some embodiments, wherein the solid tumor is head and neck cancer, the method comprises administering to a patient in need of such treatment a combination of MLN4924 or a pharmaceutically acceptable salt thereof and docetaxel. In some embodiments, wherein the solid tumor is squamous head and neck cancer, the method comprises administering to a patient in need of such treatment a combination of MLN4924 or a pharmaceutically acceptable salt thereof and docetaxel. In some embodiments, wherein the solid tumor is salivary gland cancer, the method comprises administering to a patient in need of such treatment a combination of MLN4924 or a pharmaceutically acceptable salt thereof, and docetaxel.

In some embodiments, wherein the solid tumor is cholangiocarcinoma, the method comprises administering to a patient in need of such treatment a combination of MLN4924 or a pharmaceutically acceptable salt thereof and a taxane. In some embodiments, wherein the solid tumor is cholangiocarcinoma, the method comprises administering to a patient in need of such treatment a combination of MLN4924 or a pharmaceutically acceptable salt thereof and docetaxel.

In some embodiments, wherein the solid tumor is head and neck cancer, the method comprises administering to a patient in need of such treatment a combination of MLN4924 or a pharmaceutically acceptable salt thereof, a taxane and a platin. In some embodiments, wherein the solid tumor is head and neck cancer, the method comprises administering to a patient in need of such treatment a combination of MLN4924 or a pharmaceutically acceptable salt thereof, paclitaxel and carboplatin. In some embodiments, wherein the solid tumor is squamous head and neck cancer, the method comprises administering to a patient in need of such treatment a combination of MLN4924 or a pharmaceutically acceptable salt thereof, paclitaxel and carboplatin. In some embodiments, wherein the solid tumor is salivary gland cancer, the method comprises administering to a patient in need of such treatment a combination of MLN4924 or a pharmaceutically acceptable salt thereof, paclitaxel and carboplatin.

Therapeutic Substance; Pharmaceutical Compositions.

Any of therapeutic agents described herein can be in the form of a pharmaceutically acceptable salt. In some embodiments, such salts are derived from inorganic or organic acids or bases. For reviews of suitable salts, see, e.g., Berge et al., *J. Pharm. Sci.*, 1977, 66, 1-19 and *Remington: The Science and Practice of Pharmacy*, 20th Ed., A. Gennaro (ed.), Lippincott Williams & Wilkins (2000).

Examples of suitable acid addition salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts; alkali metal salts, such as sodium and potassium salts; alkaline earth metal salts, such as calcium and magnesium salts; salts with organic bases, such as dicyclohexylamine salts, N-methyl-D-glucamine; and salts with amino acids such as arginine, lysine, and the like.

For example, Berge lists the following FDA-approved commercially marketed salts: anions acetate, besylate (benzenesulfonate), benzoate, bicarbonate, bitartrate, bromide, calcium edetate (ethylenediaminetetraacetate), camsylate (camphorsulfonate), carbonate, chloride, citrate, dihydrochloride, edetate (ethylenediaminetetraacetate), edisylate (1,2-ethanedisulfonate), estolate (lauryl sulfate), esylate (ethanesulfonate), fumarate, gluceptate (glucoheptonate), gluconate, glutamate, glycollylarsanilate (glycollamidophenylarsonate), hexylresorcinate, hydrabamine (N,N'-di(dehydroabietyl)ethylenediamine), hydrobromide, hydrochloride, hydroxynaphthoate, iodide, isethionate (2-hydroxyethanesulfonate), lactate, lactobionate, malate, maleate, mandelate, mesylate (methanesulfonate), methylbromide, methylnitrate, methylsulfate, mucate, napsylate (2-naphthalenesulfonate), nitrate, pamoate (embonate), pantothenate, phosphate/diphosphate, polygalacturonate, salicylate, stearate, subacetate, succinate, sulfate, tannate, tartrate, teoclate (8-chlorotheophyllinate) and triethiodide; organic cations benzathine (N,N'-dibenzylethylenediamine), chloroprocaine, choline, diethanolamine, ethylenediamine, meglumine (N-methylglucamine) and procaine; and metallic cations aluminum, calcium, lithium, magnesium, potassium, sodium and zinc.

Berge additionally lists the following non-FDA-approved commercially marketed (outside the United States) salts: anions adipate, alginate, aminosalicylate, anhydromethylenecitrate, arecoline, aspartate, bisulfate, butylbromide, camphorate, digluconate, dihydrobromide, disuccinate, glycerophosphate, hemisulfate, hydrofluoride, hydroiodide, methylenebis(salicylate), napadisylate (1,5-naphthalenedisulfonate), oxalate, pectinate, persulfate, phenylethylbarbiturate, picrate, propionate, thiocyanate, tosylate and undecanoate; organic cations benethamine (N-benzylphenethylamine), clemizole (1-p-chlorobenzyl-2-pyrrolildine-1'-ylmethylbenzimidazole), diethylamine, piperazine and tromethamine (tris(hydroxymethyl)aminomethane); and metallic cations barium and bismuth.

As used herein, "pharmaceutically acceptable carrier" refers to a material that is compatible with a recipient subject (a human) and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions for use in the methods of the present disclosure can be manufactured by methods well known in the art such as conventional granulating, mixing, dissolving, encapsulating, lyophilizing, or emulsifying processes, among others. Compositions can be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations can contain stabilizers, pH modifiers, surfactants, solubilizing agents, bioavailability modifiers and combinations of these.

Pharmaceutically acceptable carriers that can be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, and wool fat.

These pharmaceutical compositions are formulated for pharmaceutical administration to a human being. Such compositions can be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. In some embodiments, the compositions are administered orally, intravenously or subcutaneously. In some embodiments, the compositions are administered orally. In some embodiments, the compositions are administered intravenously. These formulations can be designed to be short-acting, fast-releasing, or long-acting. Furthermore, the compositions can be administered in a local rather than systemic means, such as administration (e.g., by injection) at a tumor site.

Pharmaceutical formulations can be prepared as liquid suspensions or solutions using a liquid, such as an oil, water, an alcohol, and combinations of these. Solubilizing agents such as cyclodextrins can be included. Pharmaceutically suitable surfactants, suspending agents, or emulsifying agents, can be added for oral or parenteral administration. Suspensions can include oils, such as peanut oil, sesame oil, cottonseed oil, corn oil and olive oil. Suspension preparations can also contain esters of fatty acids such as ethyl oleate, isopropyl myristate, fatty acid glycerides and acetylated fatty acid glycerides. Suspension formulations can include alcohols, such as ethanol, isopropyl alcohol, hexadecyl alcohol, glycerol and propylene glycol; ethers, such as poly(ethyleneglycol); petroleum hydrocarbons such as mineral oil and petrolatum; and water.

Sterile injectable forms of these pharmaceutical compositions can be aqueous or oleaginous suspensions. These suspensions may be formulated according to techniques known in the art using suitable dispersing or wetting agents and suspending agents. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as sorbitan alkyl esters, such as Tweens or Spans, and other emulsifying agents or bioavailability enhancers which are commonly used in the manufacture of pharmaceutically acceptable solid, liquid, or other dosage forms can also be used for the purposes of formulation. Compounds can be formulated for parenteral administration by injection such as by bolus injection or continuous infusion. A unit dosage form for injection can be in ampoules or in multi-dose containers.

These pharmaceutical compositions can be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents can also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes, e.g., to mask taste, to affect the site of dissolution or absorption, or to prolong drug action. Coatings can be applied to a tablet or to granulated particles for use in a capsule.

Alternatively, these pharmaceutical compositions can be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

These pharmaceutical compositions can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches can also be used. For topical applications, the pharmaceutical compositions can be formulated in a suitable ointment containing the active component suspended or dissolved in one or more carriers. Carriers for topical administration of the compounds of the present disclosure include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active component(s) suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions can be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions can be formulated in an ointment such as petrolatum.

The pharmaceutical compositions can also be administered by nasal aerosol or inhalation. Such compositions are prepared according to techniques well known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

The methods of the present disclosure are directed to treating diseases, disorders and conditions in which inhibition of NAE enzyme activity is detrimental to survival and/or expansion of diseased cells or tissue (e.g., cells are sensitive to NAE inhibition; inhibition of NAE activity disrupts disease mechanisms; reduction of NAE activity stabilizes protein which are inhibitors of disease mechanisms; reduction of NAE activity results in inhibition of proteins which are activators of disease mechanisms). The diseases, disorders and conditions are also intended to include those which require effective cullin and/or ubiquitination activity, which activity can be regulated by diminishing NAE enzyme activity.

In some embodiments, the methods of the present disclosure further comprise administering a anti-cancer agent. As used herein, the term "anticancer agent" refers to any agent that is administered to a subject with cancer for purposes of treating the cancer. The administration of the further anti-cancer agent includes administration concurrently or sequentially with the combinations of the present disclosure. Alternatively, the further anti-cancer agent can be combined into one composition with the combinations of the present disclosure which is administered to the patient.

Non-limiting examples of anti-cancer agents include DNA damaging chemotherapeutic agents such as topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, pemetrexed, mitomycin C, and cyclophosphamide); DNA intercalators; DNA intercalators and free radical generators such as bleomycin; and nucleoside mimetics (e.g., 5-fluorouracil, capecitibine, fludarabine, cytarabine, mercaptopurine, thioguanine, pentostatin, and hydroxyurea). Chemotherapeutic agents that disrupt cell replication include: vincristine, vinblastin, and related analogs; thalidomide, lenalidomide, and related analogs (e.g., CC-5013 and CC-4047); protein tyrosine kinase inhibitors (e.g., imatinib mesylate, erlotonib, croztinib and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, panitumumab, rituximab, cetuximab, and bevacizumab); and other inhibitors of proteins or enzymes known to be upregulated, over-expressed or activated in cancers, the inhibition of which downregulates cell replication.

Kits

In some embodiments, one or more of the therapeutic agents described herein can be manufactured for inclusion in a kit. A "kit" is any article of manufacture (e.g., a package or container) comprising at least one reagent or chemotherapeutic agent. A kit for use in the methods herein can comprise an NAE inhibitor, such as MLN4924 or a pharmaceutically acceptable salt thereof. In some embodiments, the kit can further include a taxane. In some embodiments, the kit can further include a platin. In some embodiments, the kit can further include gemcitabine. In some embodiments, the kit can further include a taxane and a platin. In some embodiments, the kit can include MLN4924 or a pharmaceutically acceptable salt thereof and docetaxel. In some embodiments, the kit can include MLN4924 or a pharmaceutically acceptable salt thereof and cisplatin. In some embodiments, the kit can include MLN4924 or a pharmaceutically acceptable salt thereof and carboplatin. In some embodiments, the kit can include MLN4924 or a pharmaceutically acceptable salt thereof, carboplatin and paclitaxel.

In some embodiments, a kit for use in treating lung cancer can include MLN4924 or a pharmaceutically acceptable salt thereof and docetaxel. In some embodiments, a kit for use in treating non-small cell lung cancer can include MLN4924 or a pharmaceutically acceptable salt thereof and docetaxel. In some embodiments, a kit for use in treating squamous non-small cell lung cancer can include MLN4924 or a pharmaceutically acceptable salt thereof and docetaxel. In some embodiments, a kit for use in treating head and neck cancer can include MLN4924 or a pharmaceutically acceptable salt thereof and docetaxel. In some embodiments, a kit for use in treating salivary gland cancer can include MLN4924 or a pharmaceutically acceptable salt thereof and docetaxel. In some embodiments, a kit for use in treating squamous head and neck cancer can include MLN4924 or a pharmaceutically acceptable salt thereof and docetaxel. In some embodiments, a kit for use in treating cholangiocarcinoma can include MLN4924 or a pharmaceutically acceptable salt thereof and docetaxel.

In some embodiments, a kit for use in treating lung cancer can include MLN4924 or a pharmaceutically acceptable salt thereof, paclitaxel and carboplatin. In some embodiments, a kit for use in treating non small cell lung cancer can include MLN4924 or a pharmaceutically acceptable salt thereof, paclitaxel and carboplatin. In some embodiments, a kit for use in treating squamous non small cell lung cancer can include MLN4924 or a pharmaceutically acceptable salt thereof, paclitaxel and carboplatin. In some embodiments, a kit for use in treating head and neck cancer can include MLN4924 or a pharmaceutically acceptable salt thereof, paclitaxel and carboplatin. In some embodiments, a kit for use in treating salivary gland cancer can include MLN4924 or a pharmaceutically acceptable salt thereof, paclitaxel and carboplatin. In some embodiments, a kit for use in treating squamous head and neck cancer can include MLN4924 or a pharmaceutically acceptable salt thereof, paclitaxel and carboplatin.

In some embodiments, a kit comprising MLN4924 or a pharmaceutically acceptable salt thereof and another chemotherapeutic agent can further include another component or reagent. In some embodiments, a reagent in the kit can be a diluent for preparing the MLN4924 or a pharmaceutically acceptable salt thereof for administration. In some embodiments, a reagent in the kit can be a diluent for preparing the chemotherapeutic agent for administration. In some embodiments, a component in the kit can be a vessel for mixing the combination of MLN4924 and the chemotherapeutic agent. In some embodiments, the kit can include instructions for calculating the dose of each therapeutic component of the kit. In some embodiments, the instructions can include the Calvert formula.

In order that this present disclosure be more fully understood, the following examples are set forth. These examples are illustrative only and are not intended to limit the scope of the present disclosure in any way.

Examples

MLN4924, pharmaceutical compositions of MLN4924, processes for its synthesis, and polymorphic forms have been described previously. See, e.g., U.S. patent application Ser. No. 11/700,614 (Publ. No. 2007/0191293), Ser. No. 12/221,399 (Publ. No. 2009/0036678) and Ser. No. 12/779,331 (Publ. No. 2011/0021544) each of which is hereby incorporated by reference herein in its entirety. The hydrochloride salt of MLN4924 (((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate. HCl) was used for the experiments described below. The amounts listed reflect the amount of ((1S,2S,4R)-4-(4-((1S)-2,3-dihydro-1H-inden-1-ylamino)-7H-pyrrolo[2,3-d]-pyrimidin-7-yl)-2-hydroxycyclopentyl)methyl sulfamate used.

1. In Vitro Cell Viability Assays

General Method: Cells are grown in their respective growth media, supplemented with 10% fetal bovine serum unless otherwise noted. A549-Ham's F-12K (Kaighn's) Medium; Calu-1 and HCT-116-McCoy's 5A Medium with 1% glutamine; NCI-H69, NCI-H2, NCI-H209, NCI-H510, NCI-H526, HARA, LK-2, LUDLU-1, NCI-H2170, NCI-H520, NCI-H1299, NCI-H1703, NCI-H596, RERF-LC-Sq1, and CHAGO-K-1-RPMI 1640 Medium; EBC-1, SK-MES-1, and VMRC-LCP-Minimum Essential Medium, 0.1 mM non-essential amino acids, 1 mM sodium pyruvate; LC-1 Sq-1:1 mixture of RPMI-1640 and Ham's F12K (Kaighn's) Medium; SW900 and SW 1573-Lcibovitz's L-15 (no $CO_2$); EPLC-272H-RPMI 1640 medium, 20% heat-inactivated FBS; KNS-62-Minimum Essential Medium, 0.1 mM non-essential amino acids, 1 mM sodium pyruvate, 20% FBS; MIA PaCa-2-DMEM Medium, 10% FBS, 2.5% Horse serum, penicillin-streptomycin (pen/strep); BxPC-3-RPMI 1640 medium, 10% FBS, pen/strep; PANC1-DMEM medium, 10% FBS, pen/strep. The following number of cells are seeded per well of 384-well poly-D-lysine (PDL)-coated black, clear-bottom plates (BD BioCoat™) and allowed to adhere for 24 h at 37° C., 6% CO2: A549 and HCT116 (1000 cells/well); NCI-H69 (4000-7000); NCI-H82 (1500-2000); NCI-H209 and NCI-H510 (5000-7000); NCI-H526 (1500-2500); HARA, LK-2, CHAGO-K-1, NCI-H520, RERF-LC-Sq1, EBC-1, SK-MES-1, KNS-62, and VMRC-LCP (1000); Calu-1, EPLC-272H, and NCI-H1703 (1500); LUDLU-1, NCI-H596, SW900, SW 1573 and NCI-H2170 (2000); LC-1 Sq (4000); NCI-H1299 and MIA PaCa-2 (500); BxPC3 (750); PANC1 (1000 cells), ((1S,2S,4R)-4-(4-((1S)-2,3-Dihydro-1H-inden-1-ylamino)-7H-pyrrolo[2,3-d]pyrimidin-7-yl)-2-hydroxycyclopentyl)methyl sulfamate hydrochloride is dissolved in DMSO, and the chemotherapeutic agents are dissolved in either DMSO or PBS. The cells are treated with chemotherapeutic agents, either alone or in combination with MLN4924, at various doses for 48 h (HCT116), 72 h (A549, MIA PaCa-2, BxPC3, PANC1, HARA, LK-2, NCI-H520, RERF-LC-Sq1, EBC-1, SK-MES-1, VMRC-LCP, LUDLU-1, NCI-H2170, LC-1 Sq, CHAGO-K-1, Calu-1, EPLC-272H, KNS-62, NCI-H1299, NCI-H1703, NCI-H596, SW 1573, and SW900), or 96 hr (NCI-H69, NCI-H82, NCI-H209, NCI-H510, NCI-H526). A portion of each plate is used for positive controls (no agent is added), while another portion of each plate is used for negative controls (no cells are added). Viability is assessed with CellTiter-Glo® Cell Viability reagent used according to manufacturer's instructions (Promega). Luminescence is measured using a LEADseeker imaging system (GE Healthcare).

Statistical Analyses

Normalization.

The viability data is normalized separately for each plate by scaling the data so that the median of the negative controls is 0 and the median of the positive controls is 100. More formally, $$V_i = 100 \frac{U_i - \mathrm{median}(U_-)}{\mathrm{median}(U_+) - \mathrm{median}(U_-)}$$

where $V_i$ is the normalized viability of the $i^{th}$ well, $U_i$ is the raw viability measurement, median $(U_-)$ is the median of the negative controls, and median $(U_+)$ is the median of the positive controls. After normalization, the controls are discarded.

Response Surface Model and Fitting.

A response surface model similar to that of Minto et al. (C. F. Minto, et al., *Anesthesiology*, 2000, 92, 1603-1616) is used to describe the relationship between the normalized viability and MLN4924 and chemotherapeutic agent concentrations. For a given plate, let $$C=(C_A/I_1)+(C_B/I_2)$$

$$x=(C_A/I_1)/C$$

$$E_{max}=E_1+E_2x+E_3x^2+E_4x^3$$

$$I=1+I_3x(1-x)$$

$$S=S_1+S_2x+S_3x^2+S_4x^3$$

$$V=100-E_{max}(1+(I/C)^S)^{-1}+\mathrm{error}$$

where $E_1$, $E_2$, $E_3$, $E_4$, $I_1$, $I_2$, $I_3$, $S_1$, $S_2$, $S_3$, and $S_4$ are parameters, $C_A$ and $C_B$ are the respective concentrations of agents A and B, and V is the normalized viability measurement. It is assumed that the error values are independent and identically distributed normal random variables. This model is an extension of the Hill equation (A. V. Hill, *J. Physiol.*, 1910, 40, iv-vii), which is commonly used to model the effect of a single agent. The data are fitted to this model using the maximum likelihood method with the statistical software program R (R Development Core Team, 2008, ISBN 3-900051-07-0, see, e.g., the R-Project for Statistical Computing website maintained by The R Foundation for Statistical Computing, hosted by Vienna University of Economics and Business, Vienna, Austria).

Quality Check.

Three types of quality checks are applied to the plates. First, it is checked that the variation of the positive controls and the mean of the negative controls are small. Next, it is checked that new data agreed with data from previous single agent experiments. Finally, the residuals from the response surface fit are analyzed to ensure that the residual sum of squares is sufficiently small. All of these quality checks are based on numerical thresholds to make pass/fail decisions, and the same thresholds are used for all of the plates in the experiment. If a plate failed any one of the quality checks, it is removed from the analysis.

Measuring Synergy and Additivity.

The Combination Index (T. C. Chou and P. Talalay, *Adv. Enzyme Regul.*, 1984, 22:27-55) and Nonlinear Blending (J. J. Peterson and S. J. Novik, *Journal of Receptors and Signal Transduction*, 2007, 27:125-146.) are used as measures of agent synergy. The Combination Index is computed based on an isobologram, which is a slice of the dose response surface with constant viability. For the present analysis, the 50% isobologram, which is the dose contour that has 50% viability, is used. The $EC50_A$ and $EC50_B$ are defined be the respective doses of agents A and B alone that have a viability of 50%. For a point $(D_A, D_B)$ along the 50% isobologram, the Combination Index is defined as $(D_A/EC50_A)+(D_B/EC50_B)$. Since the choice of $(D_A, D_B)$ can be arbitrary, the constraint $D_A/D_B=EC50_A/EC50_B$ is used.

In some cases, the Combination Index cannot be computed because the $EC50_A$ or $EC50_B$ does not exist. In such cases, Nonlinear Blending can be used as an alternative measure of synergy or additivity. Nonlinear Blending is found by considering a slice of the dose response surface that intersects both concentration axes and runs parallel to the viability axis. Let $V_A$ and $V_B$ be the viability where the slice intersects the drug A and B axes, respectively. Let $V_{max}$ and $V_{min}$ be the maximum and minimum viabilities along the slice. Let $$NLB_S = \min(V_A, V_B) - V_{min}$$

$$NLB_A = V_{max} - \max(V_A, V_B)$$

Define the Nonlinear Blending value to be $NLB_S$ if $NLB_S > NLB_A$ and $-NLB_A$ otherwise. Since the choice of the slice is arbitrary, the slice between the EC50 values (or the highest dose values, if the EC50s did not exist) of each drug alone is chosen. The standard error for both the Combination Index and the Nonlinear Blending are found using the Cramer-Rao lower bound (H Cramer, 1946. Mathematical Methods of Statistics; C. R. Rao, *Bulletin of the Calcutta Mathematical Society*, 1945, 37: 81-89).

Summarizing Replicates.

After completing the analysis of individual plates, the results are combined across the replicates. For a given measure and a set of replicates, the overall mean and standard error are computed using weighted averaging. A null mean, which corresponded to an additive effect, is then compared with the overall mean. The null mean is 1 for the Combination Index and 0 for Nonlinear Blending. Next, a two sized Z-test is performed based on the estimated mean and standard error. This produces a p-value for each measure and each cell line.

After computing the mean, standard error, and p-value for each set of replicates, these values require interpretation. Thus, a standard procedure is used to produce a classification (synergy, additivity, subadditivity, antagonism, or inconclusive) in each case. If the Combination Index exists for more than half of the replicates, then these measures are used to make the classification. If the Combination Index does not exist for a majority of the replicates, then a similar procedure based on Nonlinear Blending is used to make the classification.

Consider the case where the Combination Index is used to make the classification. If the p-value is greater than 0.05, the estimate for the Combination Index is not statistically different from 1. However, if the standard error is also very large, then the estimate is too uncertain to be informative. Hence, the classification is "Inconclusive". Otherwise, the classification is "Additivity". When the p-value is less than 0.05, the estimate for the Combination Index is statistically different from 1. However, if the mean is still close to 1, then the difference is not of practical significance. Thus, the result is classified based on the mean. A mean in the range (0.8, 1.2) is considered close enough to 1 to be classified as Additivity. A mean in the range (0, 0.8) is considered low enough to be classified as Synergy. A mean in the range (1.2, 2) is classified as Subadditivity because it indicates that combining the agents reduces the viability, but the reduction is less than what is predicted by the additive model. The threshold value of 2 can be derived from the definition of the Combination Index. A mean greater than 2 indicates that combining the agents increases the viability, so the combination is classified as Antagonism. Table 1 summarizes the decision rules for classifying the result based on the Combination Index. For the cases where Nonlinear Blending is used to classify the result, Table 2 describes a similar set of decision rules.

TABLE 1

Interpreting Combination Index. The Combination Index result is classified based on the p-value, the standard error, and the mean.

| P-value | Standard error | Mean | Classification |
| --- | --- | --- | --- |
| >0.05 | >0.25 | Any | Inconclusive |
| >0.05 | <0.25 | Any | Additivity |
| <0.05 | Any | 0.8 to 1.2 | Additivity |
| <0.05 | Any | 0 to 0.8 | Synergy |
| <0.05 | Any | 1.2 to 2 | Subadditivity |
| <0.05 | Any | >2 | Antagonism |

TABLE 2

Interpreting Nonlinear Blending. The Nonlinear Blending result is classified in a manner similar to the Combination Index.

| P-value | Standard error | Mean | Call |
| --- | --- | --- | --- |
| >0.05 | >15 | Any | Inconclusive |
| >0.05 | <15 | Any | Additivity |
| <0.05 | Any | −15 to 15 | Additivity |
| <0.05 | Any | >15 | Synergy |
| <0.05 | Any | <−15 | Antagonism |

Results:

Cell viability assays performed according to the general method described above were used to assess the combination effect in vitro of MLN4924 (((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate hydrochloride; MLN4924 HCl was used in all experiments) with docetaxel, paclitaxel, gemcitabine, carboplatin, cisplatin, or oxaliplatin as outlined in Table 3. Gemcitabine combinations were evaluated in 6 cell lines (HCT116 colon; A549 NSCLC; and 3 pancreatic cell lines (PANC1, MIA PaCa-2, and BxPC3). Docetaxel, paclitaxel, cisplatin, carboplatin, and oxaliplatin were evaluated in HCT116, A549, and a selection of small cell lung cancer lines (SCLC) including NCI-H209, NCI-H510, NCI-H526, NCI-H82 and NCI-H69. Carboplatin was also evaluated in 19 additional NSCLC lines, some of which are classified as squamous NSCLC. The results were statistically analyzed as described above and the analysis are summarized in Table 3, which lists the Combination Index, Nonlinear Blending Score, and classification for the interaction which was assigned as described above and in Tables 1 and 2.

TABLE 3

Summary of the in vitro combination analysis

Table 3a: Taxane-based combinations

| Agent | Cell line | Vehicle | Treatment time (hr) | Replicate experiments | Combination Index | Nonlinear Blending | Classification |
|---|---|---|---|---|---|---|---|
| docetaxel | A549 | DMSO | 72 | 1 | 1.00 ± 0.1 | 1 ± 1 | Additivity |
| docetaxel | HCT116 | DMSO | 48 | 1 | 1.01 ± 0.09 | 7 ± 2 | Additivity |
| docetaxel | NCI-H209 | DMSO | 96 | 1 | 1.27 ± 0.09 | −16 ± 5 | Subadditivity |
| docetaxel | NCI-H510 | DMSO | 96 | 1 | 1.15 ± 0.08 | −13 ± 4 | Additivity |
| docetaxel | NCI-H526 | DMSO | 96 | 1 | 1.38 ± 0.06 | −23 ± 3 | Subadditivity |
| docetaxel | NCI-H82 | DMSO | 96 | 1 | 1.45 ± 0.09 | −11 ± 2 | Subadditivity |
| paclitaxel | A549 | DMSO | 72 | 2 | 1.31 ± 0.07 | −6 ± 0.9 | Subadditivity |
| paclitaxel | HCT116 | DMSO | 48 | 4 | 1.44 ± 0.09 | −14 ± 2 | Subadditivity |
| paclitaxel | NCI-H209 | DMSO | 96 | 1 | 1.11 ± 0.07 | −8 ± 3 | Additivity |
| paclitaxel | NCI-H510 | DMSO | 96 | 1 | 1.29 ± 0.08 | −22 ± 4 | Subadditivity |
| paclitaxel | NCI-H526 | DMSO | 96 | 1 | 1.51 ± 0.08 | −26 ± 3 | Subadditivity |
| paclitaxel | NCI-H69 | DMSO | 96 | 1 | 2.20 ± 0.5 | −16 ± 4 | Antagonism |
| paclitaxel | NCI-H82 | DMSO | 96 | 1 | 1.67 ± 0.1 | −16 ± 2 | Subadditivity |

Table 3a: Combination of MLN4924 with docetaxel or paclitaxel demonstrated additivity or subadditivity in 6 of 7 cell lines tested, with the exception of NCI-H69, in which the combination of MLN4924 and paclitaxel was antagonistic.

Table 3b: gemcitabine combinations

| Agent | Cell line | Vehicle | Treatment time (hr) | Replicate experiments | Combination Index | Nonlinear Blending | Classification |
|---|---|---|---|---|---|---|---|
| gemcitabine | A549 | DMSO | 72 | 2 | 1.44 ± 0.07 | −16 ± 3 | Subadditivity |
| gemcitabine | HCT116 | DMSO | 48 | 3 | 0.49 ± 0.1 | 30 ± 3 | Synergy |
| gemcitabine | PANC1 | DMSO | 72 | 1 | 0.24 | 19.4 | Synergy |
| gemcitabine | BxPC3 | DMSO | 72 | 1 | 1.49 | −26.0 | Subadditivity |
| gemcitabine | MIA PaCa-2 | DMSO | 72 | 1 | 1.15 | −8.1 | Additivity |

Table 3b. Combination of MLN4924 with gemcitabine demonstrated synergy in the HCT116 and PANC1 cell lines, additivity in the MIA PaCa-2 and subadditivity in the A549 and BxPC3 cell lines.

Table 3c: platin-based combinations

| Agent | Cell line | Vehicle | Treatment time (hr) | Replicate experiments | Combination Index | Nonlinear Blending | Classification |
|---|---|---|---|---|---|---|---|
| carboplatin | A549 | PBS | 72 | 3 | 0.72 ± 0.05 | 8 ± 4 | Synergy |
| carboplatin | HCT116 | PBS | 48 | 2 | 0.71 ± 0.03 | 19 ± 2 | Synergy |
| carboplatin | NCI-H209 | DMSO | 96 | 1 | 1.00 ± 0.09 | −1 ± 1 | Additivity |
| carboplatin | NCI-H510 | DMSO | 96 | 1 | 0.81 ± 0.08 | 5 ± 2 | Additivity |
| carboplatin | NCI-H526 | DMSO | 96 | 1 | 1.02 ± 0.1 | 0 ± 2 | Additivity |
| carboplatin | NCI-H69 | DMSO | 96 | 2 | 1.18 ± 0.09 | −5 ± 1 | Additivity |
| carboplatin | NCI-H82 | DMSO | 96 | 1 | 0.65 ± 0.1 | 12 ± 2 | Synergy |
| cisplatin | A549 | DMSO | 72 | 3 | 0.65 ± 0.03 | 11 ± 5 | Synergy |
| cisplatin | A549 | PBS | 72 | 2 | 0.75 ± 0.05 | 10 ± 1 | Synergy |
| cisplatin | HCT116 | DMSO | 48 | 2 | 0.76 ± 0.02 | 21 ± 1 | Synergy |
| cisplatin | HCT116 | PBS | 48 | 2 | 0.76 ± 0.09 | 14 ± 6 | Synergy |
| cisplatin | NCI-H209 | DMSO | 96 | 1 | 1.28 ± 0.08 | −15 ± 3 | Subadditivity |
| cisplatin | NCI-H510 | DMSO | 96 | 1 | NA | 20 ± 3 | Synergy |
| cisplatin | NCI-H69 | DMSO | 96 | 1 | 1.28 ± 0.2 | −7 ± 3 | Additivity |
| cisplatin | NCI-H82 | DMSO | 96 | 1 | 0.81 ± 0.07 | 10 ± 2 | Additivity |
| oxaliplatin | A549 | PBS | 72 | 3 | 0.96 ± 0.06 | 2 ± 2 | Additivity |
| oxaliplatin | HCT116 | PBS | 48 | 3 | 0.81 ± 0.09 | 10 ± 5 | Additivity |
| oxaliplatin | NCI-H209 | DMSO | 96 | 1 | 1.12 ± 0.08 | −5 ± 2 | Additivity |
| oxaliplatin | NCI-H510 | DMSO | 96 | 1 | 0.94 ± 0.09 | 2 ± 3 | Additivity |
| oxaliplatin | NCI-H526 | DMSO | 96 | 1 | 1.13 ± 0.09 | −8 ± 4 | Additivity |
| oxaliplatin | NCI-H69 | DMSO | 96 | 1 | 0.69 ± 0.1 | 11 ± 3 | Synergy |
| oxaliplatin | NCI-H82 | DMSO | 96 | 1 | 0.85 ± 0.07 | 6 ± 2 | Additivity |
| carboplatin | CALU-1 | PBS | 72 | 7 | 0.78 ± 0.05 | 11 ± 6 | Synergy |
| carboplatin | CHAGO-K-1 | PBS | 72 | 2 | 0.88 ± 0.03 | 11 ± 1 | Additivity |
| carboplatin | EBC-1 | PBS | 72 | 2 | 1.24 ± 0.06 | −7 ± 1 | Subadditivity |
| carboplatin | EPLC-272H | PBS | 72 | 3 | 1.62 ± 0.03 | −37 ± 2 | Subadditivity |
| carboplatin | HARA | PBS | 72 | 5 | 1.06 ± 0.1 | −3 ± 10 | Additivity |
| carboplatin | KNS-62 | PBS | 72 | 4 | 0.82 ± 0.1 | 10 ± 5 | Additivity |
| carboplatin | LC-1-SQ | PBS | 72 | 2 | 0.51 ± 0.04 | 28 ± 2 | Synergy |
| carboplatin | LK-2 | PBS | 72 | 2 | 0.66 ± 0.05 | 15 ± 2 | Synergy |
| carboplatin | LUDLU-1 | PBS | 72 | 3 | 0.84 ± 0.2 | 5 ± 5 | Additivity |
| carboplatin | NCI-H1299 | PBS | 72 | 2 | 1.10 ± 0.05 | −8 ± 2 | Additivity |
| carboplatin | NCI-H1703 | PBS | 72 | 2 | 1.31 ± 0.02 | −23 ± 2 | Subadditivity |
| carboplatin | NCI-H2170 | PBS | 72 | 3 | 1.38 ± 0.1 | −19 ± 7 | Subadditivity |

TABLE 3-continued

Summary of the in vitro combination analysis

| carboplatin | NCI-H520 | PBS | 72 | 2 | NA | 9 ± 20 | Inconclusive |
|---|---|---|---|---|---|---|---|
| carboplatin | NCI-H596 | PBS | 72 | 3 | 0.59 ± 0.1 | 10 ± 7 | Synergy |
| carboplatin | RERF-LC-SQ1 | PBS | 72 | 3 | 0.77 ± 0.06 | 11 ± 1 | Synergy |
| carboplatin | SK-MES-1 | PBS | 72 | 2 | 1.32 ± 0.06 | −22 ± 4 | Subadditivity |
| carboplatin | SW1573 | PBS | 72 | 2 | NA | 6 ± 5 | Additivity |
| carboplatin | SW900 | PBS | 72 | 2 | 0.85 ± 0.06 | 10 ± 1 | Additivity |
| carboplatin | VMRC-LCP | PBS | 72 | 3 | 1.00 ± 0.04 | −3 ± 1 | Additivity |

Table 3c. Platin-based combinations with MLN4924: Combination of MLN4924 with carboplatin demonstrates synergy in 6 NSCLC cell lines (4 of which are squamous NSCLC), 1 colon, and 1 SCLC cell line, additivity in 4 other SCLC lines, additivity in 8 other NSCLC cell lines (7 of which are squamous NSCLC) and sub-additivity in 5 other NSCLC cell lines (3 of which are squamous NSCLC). Combination results for MLN4924 with carboplatin in 1 additional sqNSCLC cell line were inconclusive. Squamous NSCLC samples display 3q amplification in up to 94% of identified cases (Belvedere et al., Genomics, 2012; 99: 18-24). The following NSCLC cell lines did not demonstrate 3q amplification and thus may not represent squamous cell lines: A549, Calu-1, NCI-H2170, SK-MES-1, and SW900. Combination of MLN4924 with cisplatin demonstrates synergy in a NSCLC, colon, and SCLC line, with additivity or subadditivity in 3 other SCLC lines evaluated. Combination of MLN4924 with oxaliplatin demonstrates synergy in one SCLC line and additivity in a NSCLC, colon and 4 other SCLC lines. Each of the platin-based agents therefore demonstrated synergy with MLN4924 in at least one cell line.

2. In Vive Tumor Efficacy Models

Tumor Models:

The PHTX02B breast xenograft model was established from a patient-derived tumor collected during surgery from a 51 year female with invasive ductal carcinoma classified as triple negative breast cancer (ER−/PR−/Her2−) by IHC. PHTX02B tumor fragments (approximately 2×2×3 mm$^3$) are implanted into the subcutaneous space in the right dorsal flank of female SCID-NOD mice (age 5-7 weeks, Jackson Laboratory, Bar Harbor, Me.) using a 13-gauge trocar.

NCI-H1650 (2×10$^6$) tumor cells in RPMI-1640 media are mixed with an equal volume of Matrigel (BD Biosciences) and aseptically injected into the subcutaneous space in the right dorsal flank of Balb/c Nude mice (age 4-6 weeks, Shanghai SINO-British SIPPR/BK Lab Animal Ltd.) using a 25-gauge needle.

NCI-H69 or NCI-H82 small cell lung tumor fragments (30- to 40-mg) are implanted into the subcutaneous space in the area of the right flank of NCr nu/nu mice (7-10 weeks, Charles River Laboratories, Inc, Frederick Md. or Wilmington, Mass.) using a 12-gauge trocar.

The PHTX249 Pa pancreatic xenograft model was established from a patient-derived tumor collected during surgery from a 63 year female with pancreatic adenocarcinoma. PHTX249 Pa tumor fragments (approximately 2×2×3 mm$^3$) are implanted into the subcutaneous space in the right dorsal flank of female CB-17 SCID mice (7-8 weeks, Taconic Farms, Inc., Cambridge City, Ind.) using a 13-gauge trochar.

LU1143 squamous non small cell lung cancer tumor fragments (approximately 2×2×3 mm$^3$) are implanted into the subcutaneous space in the flank of female BALB/C Nude mice (5 weeks, Shanghai Laboratory Animal Center, Shanghai, China).

LXFE409 squamous non small cell lung cancer tumor fragments are implanted into the subcutaneous space in the flank of female NMRI nu/nu mice (5-7 weeks, Janvier Labs, Saint Berthevin, France).

Test Agents:

All chemotherapeutic agents were clinical grade purchased from commercial sources and are administered as outlined below.

Docetaxel (Henry Schein, Inc., Pittsburgh Pa., Qilu Pharmaceutical Co., Ltd., Jinan, Shandong, China, and Sanofi-Aventis) is formulated in 0.9% saline and administered by intravenous injection (IV) once weekly (QW) at 5 mg/kg or 10 mg/kg.

Gemcitabine (Gemzar, Henry Schein, Inc, Pittsburgh Pa., and Myoderm Medical, Norristown, Pa.) is formulated in 0.9% saline and administered by intraperitoneal injection (IP) q3Dx4 (every 3 days for a total of 4 doses) at 2.5 mg/kg or 10 mg/kg, or by IV injection twice weekly (BIW) at 20 mg/kg IVU.

Cisplatin (PCH PHARMACHEMIE) is formulated in 0.9% saline and administered by IP injection q4Dx3 (every 4 days for a total of 3 doses) at 2 mg/kg or 4 mg/kg.

Carboplatin (CARBOplatin Injection, Hospira, Inc., Qilu Pharmaceutical Co., Ltd. Jinan, Shandong, China, and Teva Gry-Pharma GmbH, Ulm, Germany) is formulated in 0.9% saline and administered by IP injection once weekly (QW) at 50 mg/kg. The once weekly schedule is also described as every 7 days (Q7D).

MLN4924 (MLN4924 hydrochloride salt; (((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate hydrochloride) is formulated in 10% HPbCD or 20% HPbCD in sterile water and administered by subcutaneous injection on one of the following schedules:

A. twice daily every day (BID);
B. twice daily for 5 days followed by 5 treatment-free days (BID 5 on/5 off); for example twice daily on days 1, 2, 3, 4, 5, 11, 12, 13, 14, 15
C. twice daily every 3 days for a total of 2 dosing days per week (BID Q3Dx2/week); also described as BID BIW, or twice daily on a biweekly schedule; for example twice daily on days 1, 4, 8, 11, 15, 18
D. twice daily every 2 days for a total of 3 dosing days per week (BID Q2Dx3/week); for example twice daily on days 1, 3, 5, 8, 10, 12, 15, 17, 19
E. once daily every 2 days for a total of 3 dosing days per week (Q2Dx3/week); also described as three times a week (TIW); for example once daily on days 1, 3, 5, 8, 10, 12, 15, 17, 19.

Tumor Measurements:

Tumors are measured twice weekly using a vernier caliper. Tumor volumes are calculated using standard procedures (0.5×(length×width$^2$)). When the tumors reach a volume of approximately 130 mm$^3$ (LXFE409), 150 mm$^3$ (NCI-H1650, NCI-H69, NCI-H82), 170 mm$^3$ (LU1143), 200 mm$^3$ (PHTX02B), or 225 mm$^3$ (PHTX249 Pa), mice are randomized into groups of 6-10 as described in the tables below, and injected with vehicle, MLN4924 (((1S,2S,4R)-4-(4-((1S)-2,3-dihydro-1H-inden-1-ylamino)-7H-pyrrolo[2, 3-d]pyrimidin-7-yl)-2-hydroxycyclopentyl)methyl sulfamate hydrochloride salt; MLN4924 HCl was used in all experiments) or one of the agents (gemcitabine, docetaxel, cisplatin, or carboplatin), or the combination of MLN4924 and one of the agents, at various doses and schedules as described below in Tables 4-9. Tumor size and body weight are measured approximately twice a week for the duration of the study. Mice are euthanized when their tumor volume reached 10% of their body weight, or when the average tumor volume of a treatment or control group reached approximately 2000 mm$^3$. Tumor growth continued to be monitored after the dosing period in some studies. Tumor volume on study day 18, 21 or 22 for all groups of all studies is shown in Tables 4-9. Average tumor volume is reported as a function of time for selected groups of selected studies in Figures A, B, and C.

Statistical Analyses of Combination Effect for Tumor Growth in Subcutaneous Xenograft Models.

Measurements from day 0 to 18, 21 or 22 are analyzed as specified in Tables 4-9. All tumor volumes have a value of 1 added to them before $\log_{10}$ transformation. For each animal, the log tumor volume at day 0 is subtracted from the log tumor volume on the subsequent days. This difference vs. time is used to calculate an area under the curve (AUC) for each animal using the trapezoid rule. In instances when an animal in a treatment group is removed early from the study, the last observed tumor value is carried forward through all subsequent time points. The synergy score for the combination of agents A and B is defined as $$100*(\text{mean}(AUC_{AB})-\text{mean}(AUC_A)-\text{mean}(AUC_B)+\text{mean}(AUC_{ctl}))/\text{mean}(AUC_{ctl}):$$

where $AUC_{AB}$, $AUC_A$, $AUC_B$, and $AUC_{ctl}$ are the AUC values for animals in the combination group, the A group, the B group, and the control group, respectively. The standard error of the synergy score is computed based on the variation in the AUC values among the animals. A two sided t-test is used to determine if the synergy score is significantly different from zero. If the P-value is above 0.05, then the combination is considered to be additive. If the P-value is below 0.05, and the synergy score is less than zero, then the combination is considered to be synergistic. If the P-value is below 0.05, the synergy score is greater than zero, and the combination is more effective than either agent alone, then the combination is considered to be subadditive. Otherwise, the combination is classified as antagonistic.

Results:

Mouse xenograft models, performed as described in the general methods above, were used to assess the combination effect in vivo of MLN4924 and docetaxel, MLN4924 and gemcitabine, MLN4924 and carboplatin, and MLN4924 and cisplatin. The details for each study are as shown below in Tables 4-9. The results were analyzed using the statistical analysis described above and the classification of the combination is shown below in Tables 4-9. MLN4924 hydrochloride salt; (((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate hydrochloride) was used in all experiments; the values listed in table 4-9 reflect the amounts of MLN4924.

MLN4924 and Docetaxel

In the PHTX02B breast xenograft model (shown in FIG. 1), dosing of the single agents (MLN4924 SC 60 mg/kg BID 5 days on/5 days off) and docetaxel (5 mg/kg IV QW) inhibited tumor growth compared to the control vehicle group. However, tumors in the single agent groups continued to grow in size during the treatment period. The combination treatment using these doses and schedules led to complete inhibition of tumor growth with a decrease in tumor volume compared to the starting volume. All treatment groups from the study are shown in Table 4a. The combination benefit for this combination in this study was scored as additive (Table 4b).

TABLE 4a

Combination of docetaxel and MLN4924 in PHTX02B xenograft model

| Group | Treatment | Dosing Regimen | Route | average tumor volume day 21 | SEM tumor volume day 21 | number of mice in group (number on day 21) |
|---|---|---|---|---|---|---|
| 1 | 10% HPbCD | BID | SC | 2066.3 | 87.8 | 10 |
| 2 | 30 mg/kg MLN4924 | BID | SC | 894.4 | 83 | 10 |
| 3 | 5 mg/kg docetaxel | QW | IV | 736.3 | 112.2 | 10 |
| 4 | 30 mg/kg MLN4924; 5 mg/kg docetaxel | BID; QW | SC; IV | 359.2 | 45.9 | 10 (9) |
| 5 | 30 mg/kg MLN4924 | BID 5 on/5 off | SC | 1110.9 | 150.2 | 10 |
| 6 | 30 mg/kg MLN4924; 5 mg/kg docetaxel | BID 5 on/5 off; QW | SC; IV | 444.8 | 73.5 | 10 |
| 7 | 60 mg/kg MLN4924 | BID 5 on/5 off | SC | 532.2 | 88.4 | 10 |
| 8 | 60 mg/kg MLN4924; 5 mg/kg docetaxel | BID 5 on/5 off; QW | SC; IV | 97.5 | 26.5 | 10 |

TABLE 4b

Classification for in vivo combination of docetaxel and MLN4924 in PHTX02B xenograft model

| Treatment | Synergy score (Day 21) | Synergy score standard error | P-value | Classification |
|---|---|---|---|---|
| MLN4924 30 mg/kg BID + docetaxel | 10 | 9.8 | 0.317 | additive |
| MLN4924 30 mg/kg BID 5 on/5 off + docetaxel | 11.8 | 12.6 | 0.356 | additive |
| MLN4924 60 mg/kg BID 5 on/5 off + docetaxel | −21.8 | 15.2 | 0.165 | additive |

Figure 4:
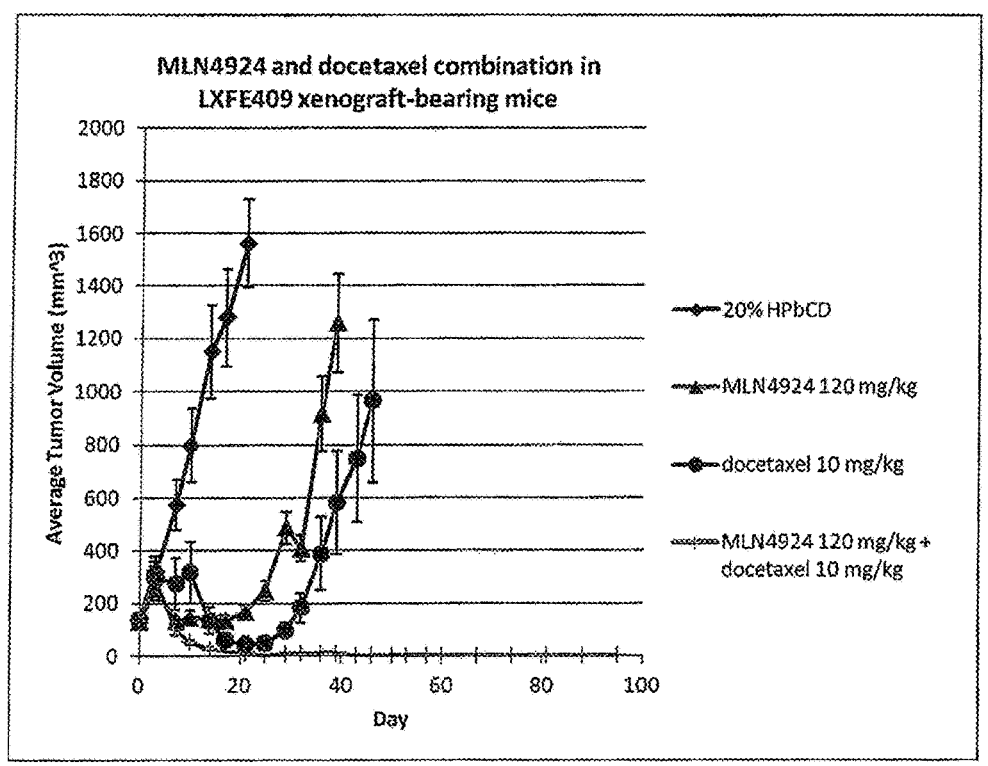
FIG. 4 shows a plot of tumor volume as a function of time in a LXFE409 xenograft model following administration of MLN4924 and docetaxel to mice.

The combination of docetaxel and MLN4924 was also evaluated in the NCI-H1650 NSCLC model, the LU1143 sqNSCLC model, and the LXFE409 sqNSCLC model and results are shown in Tables 5a-5e. In the LXFE409 sqNSCLC model, the combination of MLN4924 (120 mg/kg SC Q2Dx3/week for 3 weeks) with docetaxel (10 mg/kg IV QW for 3 weeks) resulted in tumor regression in all 8 mice treated with this regimen, and complete regressions were maintained in this combination treatment group through the end of study on day 95. In contrast, tumors treated with the single agents MLN4924 or docetaxel regrew after the treatment period ended. A graph of these results is shown in FIG. 4.

TABLE 5a

Combination of docetaxel and MLN4924 in NCI-H1650 xenograft model

| Group | Treatment | Dosing Regimen | Route | average tumor volume day 21 | SEM tumor volume day 21 | number of mice in group (number on day 21) |
|---|---|---|---|---|---|---|
| 1 | 20% HPbCD; 0.9% Saline | Q2Dx3/week; QW | SC; IV | 990.8 | 68.1 | 8 |
| 2 | 120 mg/kg MLN4924 | Q2Dx3/week | SC | 774.2 | 38.3 | 8 |
| 3 | 90 mg/kg MLN4924 | Q2Dx3/week | SC | 776.8 | 44.8 | 8 |
| 4 | 10 mg/kg docetaxel | QW | IV | 282.7 | 44.4 | 8 |
| 5 | 5 mg/kg docetaxel | QW | IV | 719.2 | 49.1 | 8 |
| 6 | 120 mg/kg MLN4924; 10 mg/kg docetaxel | Q2Dx3/week; QW | SC; IV | 154.5 | 21.8 | 8 |
| 7 | 120 mg/kg MLN4924; 5 mg/kg docetaxel | Q2Dx3/week; QW | SC; IV | 429.1 | 35.5 | 8 |
| 8 | 90 mg/kg MLN4924; 10 mg/kg docetaxel | Q2Dx3/week; QW | SC; IV | 212.8 | 44.3 | 8 |
| 9 | 90 mg/kg MLN4924; 5 mg/kg docetaxel | Q2Dx3/week; QW | SC; IV | 586.4 | 38.1 | 8 |

TABLE 5b

Classification for in vivo combination of docetaxel and MLN4924 in NCI-H1650 xenograft model

| Treatment | Synergy score (Day 21) | Synergy score standard error | P-value | Classification |
|---|---|---|---|---|
| 120 mg/kg MLN4924; 5 mg/kg docetaxel | −16.2 | 11.4 | 0.175 | additive |
| 120 mg/kg MLN4924; 5 mg/kg docetaxel | −11.5 | 7.6 | 0.145 | additive |
| 90 mg/kg MLN4924; 10 mg/kg docetaxel | −7.2 | 12.7 | 0.578 | additive |
| 90 mg/kg MLN4924; 5 mg/kg docetaxel | 1.4 | 7.5 | 0.852 | additive |

TABLE 5c

Combination of docetaxel and MLN4924 in LU1143 xenograft model

| Group | Treatment | Dosing Regimen | Route | average tumor volume day 21 | SEM tumor volume day 21 | number of mice in group (number on day 21) |
|---|---|---|---|---|---|---|
| 1 | 20% HPbCD; 0.9% saline | BID; QW | SC; IV | 996.1 | 128 | 8 |
| 2 | 45 mg/kg MLN4924 | BID | SC | 801.2 | 112.4 | 8 |
| 3 | 10 mg/kg docetaxel | QW | IV | 498.9 | 58.5 | 8 |
| 5 | 45 mg/kg MLN4924; 10 mg/kg docetaxel | BID; QW | SC; IV | 366.5 | 37.3 | 8 | ksGroups 4 and 6 from this study in the LU1143 xenograft model contained carboplatin and are presented in Table 7c. Group 1 (vehicle control) and group 2 (MLN4924) are also presented in Table 7c.

TABLE 5d

Classification for in vivo combination of docetaxel and MLN4924 in LU1143 xenograft model

| Treatment | Synergy score (Day 21) | Synergy score standard error | P-value | Classification |
|---|---|---|---|---|
| 45 mg/kg MLN4924; 10 mg/kg docetaxel | 2.8 | 11.4 | 0.808 | additive |

TABLE 5e

Combination of docetaxel and MLN4924 in LXFE409 xenograft model

| Group | Treatment | Dosing Regimen | Route | average tumor volume day 21 | SEM tumor volume day 21 | number of mice in group (number on day 21) |
|---|---|---|---|---|---|---|
| 1 | 20% HPbCD | Q2Dx3/week | SC | 1561.6 | 167.2 | 8 |
| 3 | 120 mg/kg MLN4924 | Q2Dx3/week | SC | 167.1 | 23.3 | 8 |
| 6 | 10 mg/kg docetaxel | QW | IV | 44.6 | 14.5 | 8 |
| 7 | 120 mg/kg MLN4924; 10 mg/kg docetaxel | Q2Dx3/week; QW | SC; IV | 10.3 | 4.6 | 8 |

Groups 2, 4, and 5 from this study in the LXFE409 xenograft model are relevant to the combination of MLN4924 with carboplatin and are presented in Table 7e. Group 1 (vehicle control) is also presented in Table 7e.

TABLE 5f

Classification for in vivo combination of docetaxel and MLN4924 in LXFE409 xenograft model

| Treatment | Synergy score (Day 21) | Synergy score standard error | P-value | Classification |
|---|---|---|---|---|
| 120 mg/kg MLN4924; 10 mg/kg docetaxel | 49.2 | 25 | 0.069 | additive |

MLN4924 and Gemcitabine

Figure 2:
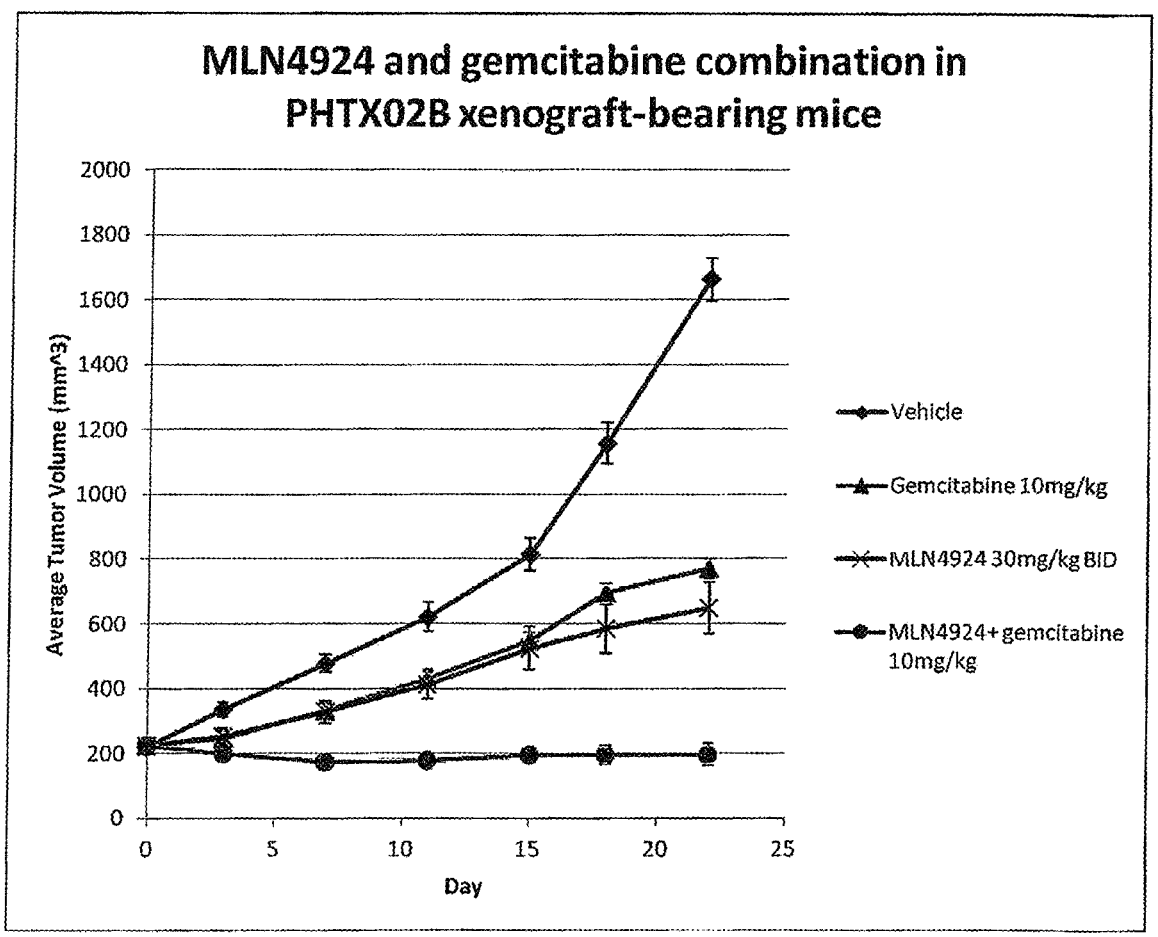
FIG. 2 shows a plot of tumor volume as a function of time in a PHTX02B xenograft model following administration of MLN4924 and gemcitabine to mice.

In the PHTX02B xenograft model (shown in FIG. 2), dosing of the single agents (MLN4924 SC 30 mg/kg BID) and gemcitabine (10 mg/kg IP q3dx4) inhibited tumor growth compared to the control vehicle group, but tumors in the single agent groups continued to grow in size during the treatment period. In contrast, the combination treatment prevented tumor growth, and tumor volume at the end of the treatment period remained the same as the starting volume. All treatment groups from the study are shown in Table 6a. The combination benefit was assessed as additive (Table 6b).

In the PHTX249 Pa xenograft model, dosing of gemcitabine (20 mg/kg IV BIW) inhibited tumor growth compared to the control vehicle group, but tumors treated with MLN4924 (90 mg/kg SC BID BIW) did not show growth inhibition compared to the control vehicle group. The combination treatment inhibited tumor growth to a similar extent as gemcitabine alone, and the combination effect was assessed as additive. Treatment groups and combination analysis are shown in Tables 6c and 6d.

TABLE 6a

Combination of gemcitabine and MLN4924 in PHTX02B xenograft model

| Group | Treatment | Dosing Regimen | Route | average tumor volume day 22 | SEM tumor volume day 22 | number of mice in group (number on day 22) |
|---|---|---|---|---|---|---|
| 1 | 10% HPbCD | BID | SC | 1661.9 | 66.9 | 10 |
| 2 | 2.5 mg/kg gemcitabine | Q3Dx4 | IP | 1386.3 | 113.9 | 10 |
| 3 | 10 mg/kg gemcitabine | Q3Dx4 | IP | 769.4 | 30.2 | 10 (9) |
| 4 | 30 mg/kg MLN4924 | BID | SC | 647.4 | 78.6 | 10 |
| 5 | 30 mg/kg MLN4924; 2.5 mg/kg gemcitabine | BID; Q3Dx4 | SC; IP | 499.5 | 66.5 | 10 |
| 6 | 30 mg/kg MLN4924; 10 mg/kg gemcitabine | BID; Q3Dx4 | SC; IP | 196.2 | 34.5 | 10 (8) |

TABLE 6b

Classification for in vivo combination of gemcitabine and MLN4924 in PHTX02B xenograft model

| Treatment | Synergy score (Day 22) | Synergy score standard error | P-value | Classification |
|---|---|---|---|---|
| 30 mg/kg MLN4924; 2.5 mg/kg gemcitabine | 0.7 | 13.4 | 0.956 | additive |
| 30 mg/kg MLN4924; 10 mg/kg gemcitabine | −21.8 | 16.1 | 0.188 | additive |

TABLE 6c

Combination of gemcitabine and MLN4924 in PHTX249Pa xenograft model

| Group | Treatment | Dosing Regimen | Route | average tumor volume day 18 | SEM tumor volume day 18 | number of mice in group (number on day 18) |
|---|---|---|---|---|---|---|
| 1 | 0.9% saline | QW | IV | 1430.4 | 183.5 | 6 |
| 2 | 20 mg/kg gemcitabine | BIW | IV | 585.1 | 85 | 6 |
| 3 | 90 mg/kg MLN4924 | BID BIW | SC | 1748.9 | 432.2 | 6 (4) |
| 4 | 90 mg/kg MLN4924; 20 mg/kg gemcitabine | BID BIW; BIW | IV; SC | 621.8 | 153.5 | 6 |

TABLE 6d

Classification for in vivo combination of gemcitabine and MLN4924 in PHTX249Pa xenograft model

| Treatment | Synergy score (Day 18) | Synergy score standard error | P-value | Classification |
|---|---|---|---|---|
| 90 mg/kg MLN4924; 20 mg/kg gemcitabine | −11.9 | 22.1 | 0.6 | additive |

MLN4924 and Platins

Figure 3:
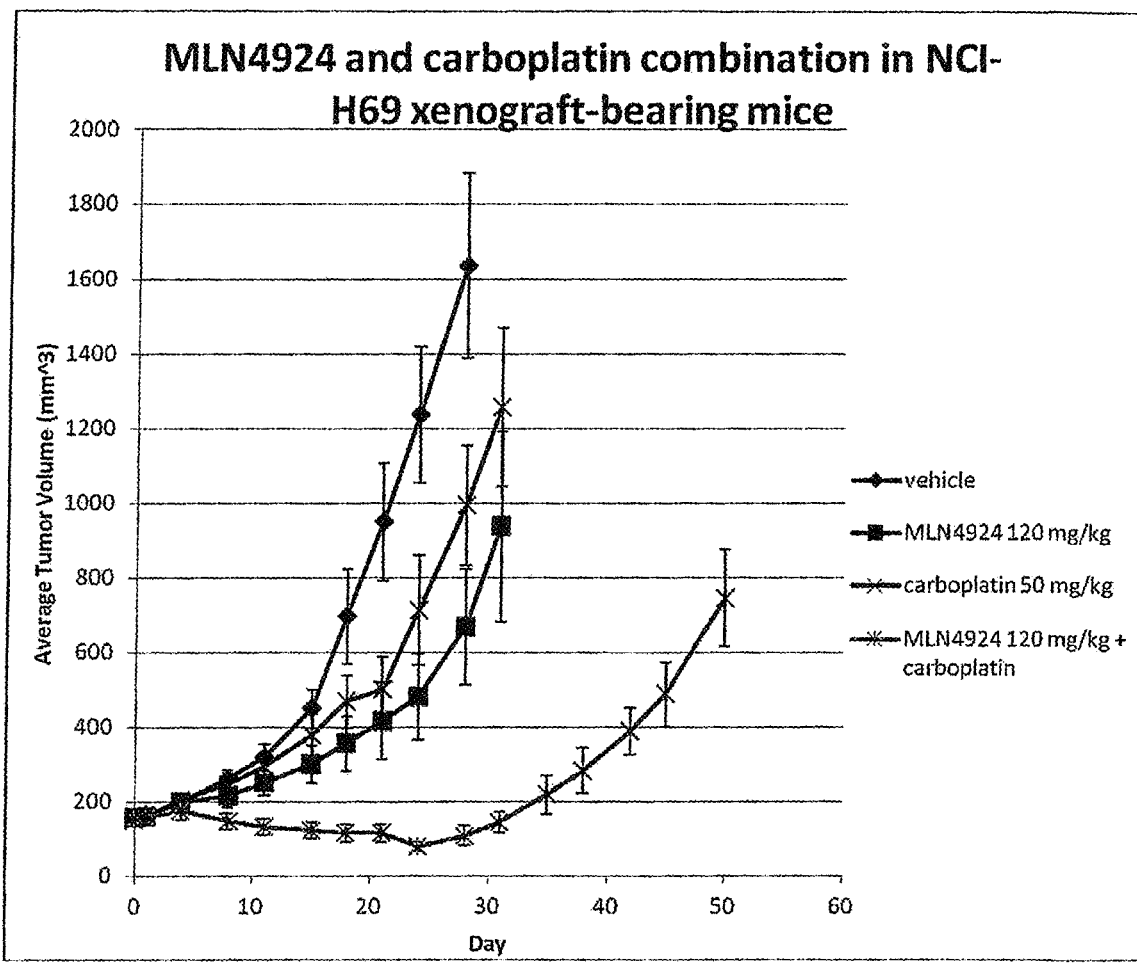
FIG. 3 shows a plot of tumor volume as a function of time in a NCI-H69 xenograft model following administration of MLN4924 and carboplatin to mice.

In the NCI-H69 xenograft model (shown in FIG. 3), dosing of the single agents (MLN4924 SC 120 mg/kg BID Q3Dx2/week) and carboplatin (50 mg/kg IP QW) inhibited tumor growth compared to the control vehicle group. However, tumors in the single agent groups continued to grow in size during the treatment period. In contrast, the combination treatment using these doses and schedules led to complete inhibition of tumor growth with a decrease in tumor volume compared to the starting volume. All treatment groups from the study are shown in Table 7a. The combination benefit for this treatment was scored as synergy (Table 7b). The combination of carboplatin and MLN4924 was further evaluated in 2 sqNSCLC xenograft models, LU1143 (Table 7c,d) and LXFE409 (Table 7e,f). The combination of cisplatin and MLN4924 was evaluated in the NCI-H69 xenograft model (Tables 8a,b) and in the NCI-H82 xenograft model (Tables 9a,b).

TABLE 7a

Combination of carboplatin and MLN4924 in NCI-H69 xenograft model

| Group | Treatment | Dosing Regimen | Route | average tumor volume day 21 | SEM tumor volume day 21 | number of mice in group (number on day 21) |
|---|---|---|---|---|---|---|
| 1 | 20% HPbCD; 0.9% saline | BID Q3D x 2/week; QW | SC; IP | 949.8 | 157.6 | 8 |
| 2 | 120 mg/kg MLN4924 | BID Q3D x 2/week | SC | 415.2 | 103.8 | 8 |
| 3 | 60 mg/kg MLN4924 | BID Q3D x 2/week | SC | 597.1 | 55.9 | 8 |
| 4 | 50 mg/kg carboplatin | QW | IP | 501.3 | 87.4 | 8 |
| 5 | 120 mg/kg MLN4924; 50 mg/kg carboplatin | BID Q3D x 2/week; QW | SC; IP | 115.2 | 23.5 | 8 |
| 6 | 60 mg/kg MLN4924; 50 mg/kg carboplatin | BID Q3D x 2/week; QW | SC; IP | 247.5 | 25.4 | 8 |

TABLE 7b

Classification for combination of carboplatin and MLN4924 in NCI-H69 xenograft model

| Treatment | Synergy score (Day 21) | Synergy score standard error | P-value | Classification |
|---|---|---|---|---|
| 120 mg/kg MLN4924; 50 mg/kg carboplatin | −63.1 | 19.8 | 0.005 | synergy |
| 60 mg/kg MLN4924; 50 mg/kg carboplatin | −43.8 | 16.5 | 0.016 | synergy |

TABLE 7c

Combination of carboplatin and MLN4924 in LU1143 xenograft model

| Group | Treatment | Dosing Regimen | Route | average tumor volume day 21 | SEM tumor volume day 21 | number of mice in group (number on day 21) |
|---|---|---|---|---|---|---|
| 1 | 20% HPbCD; 0.9% saline | BID; QW | SC; IV | 996.1 | 128 | 8 |
| 2 | 45 mg/kg MLN4924 | BID | SC | 801.2 | 112.4 | 8 |

TABLE 7c-continued

Combination of carboplatin and MLN4924 in LU1143 xenograft model

| Group | Treatment | Dosing Regimen | Route | average tumor volume day 21 | SEM tumor volume day 21 | number of mice in group (number on day 21) |
|---|---|---|---|---|---|---|
| 4 | 50 mg/kg carboplatin | QW | IP | 658.7 | 66.8 | 8 |
| 6 | 45 mg/kg MLN4924; 50 mg/kg carboplatin | BID; QW | SC; IP | 275.8 | 53.2 | 8 |

TABLE 7d

Classification for combination of carboplatin and MLN4924 in LU1143 xenograft model

| Treatment | Synergy score (Day 21) | Synergy score standard error | P-value | Classification |
|---|---|---|---|---|
| 45 mg/kg MLN4924; 50 mg/kg carboplatin | −26.3 | 16.1 | 0.118 | additive |

TABLE 7e

Combination of carboplatin and MLN4924 in LXFE409 xenograft model

| Group | Treatment | Dosing Regimen | Route | average tumor volume day 21 | SEM tumor volume day 21 | number of mice in group (number on day 21) |
|---|---|---|---|---|---|---|
| 1 | 20% HPbCD | Q2Dx3/week | SC | 1561.6 | 167.2 | 8 |
| 2 | 90 mg/kg MLN4924 | Q2Dx3/week | SC | 707.5 | 194.2 | 8 |
| 4 | 50 mg/kg carboplatin | QW | IP | 204.4 | 96.8 | 8 |
| 5 | 90 mg/kg MLN4924; 50 mg/kg carboplatin | Q2Dx3/week; QW | SC; IP | 122.5 | 54.6 | 8 |

TABLE 7f

Classification for combination of carboplatin and MLN4924 in LXFE409 xenograft model

| Treatment | Synergy score (Day 21) | Synergy score standard error | P-value | Classification |
|---|---|---|---|---|
| 90 mg/kg MLN4924; 50 mg/kg carboplatin | 37.8 | 20.4 | 0.081 | additive |

TABLE 8a

Combination of cisplatin and MLN4924 in NCI-H69 xenograft model

| Group | Treatment | Dosing Regimen | Route | average tumor volume day 22 | SEM tumor volume day 22 | number of mice in group (number on day 22) |
|---|---|---|---|---|---|---|
| 1 | 20% HPbCD; 0.9% saline | BID Q2Dx3/week; Q4Dx3 | SC; IP | 983.2 | 184.6 | 10 (9) |
| 2 | 60 mg/kg MLN4924 | BID Q2Dx3/week | SC | 475.4 | 90.6 | 10 |
| 3 | 45 mg/kg MLN4924 | BID Q3Dx2/week | SC | 438.5 | 92.8 | 10 |
| 4 | 4 mg/kg Cisplatin | Q4Dx3 | IP | 213.6 | 19.3 | 10 |
| 5 | 60 mg/kg MLN4924; 4 mg/kg cisplatin | BID Q2Dx3/week; Q4Dx3 | SC; IP | 55.3 | 10.8 | 10 |
| 6 | 45 mg/kg MLN4924; 4 mg/kg cisplatin | BID Q3Dx2/week; Q4Dx3 | SC; IP | 98.7 | 27.4 | 10 (8) |

TABLE 8b

Classification for combination of cisplatin and MLN4924 in NCI-H69 xenograft model

| Treatment | Synergy score (Day 22) | Synergy score standard error | P-value | Classification |
|---|---|---|---|---|
| 60 mg/kg MLN4924; 4 mg/kg cisplatin | −27.5 | 15.6 | 0.091 | additive |
| 45 mg/kg MLN4924; 4 mg/kg cisplatin | −1.1 | 28.2 | 0.97 | additive |

TABLE 9a

Combination of cisplatin and MLN4924 in NCI-H82 xenograft model

| Group | Treatment | Dosing Regimen | Route | average tumor volume day 22 | SEM tumor volume day 22 | number of mice in group (number on day 22) |
|---|---|---|---|---|---|---|
| 1 | 20% HPbCD; 0.9% saline | BID Q2Dx3/week; Q4Dx3 | SC; IP | 946.9 | 135.2 | 10 (9) |
| 2 | 60 mg/kg MLN4924 | BID Q2Dx3/week | SC | 861.9 | 121 | 10 |
| 3 | 60 mg/kg MLN4924 | BID Q3Dx2/week | SC | 783.3 | 97.8 | 10 |
| 4 | 4 mg/kg cisplatin | Q4Dx3 | IP | 445.2 | 57 | 10 |
| 5 | 2 mg/kg cisplatin | Q4Dx3 | IP | 628.7 | 72 | 10 (9) |
| 6 | 60 mg/kg MLN4924; 4 mg/kg cisplatin | BID Q2Dx3/week; Q4Dx3 | SC, IP | 194.4 | 65.3 | 10 (8) |
| 7 | 60 mg/kg MLN4924; 4 mg/kg cisplatin | BID Q3Dx2/week; Q4Dx3 | SC; IP | 199.1 | 39.6 | 10 (9) |
| 8 | 60 mg/kg MLN4924; 2 mg/kg cisplatin | BID Q2Dx3/week; Q4Dx3 | SC; IP | 438.3 | 49.3 | 10 (8) |
| 9 | 60 mg/kg MLN4924; 2 mg/kg cisplatin | BID Q3Dx2/week; Q4Dx3 | SC; IP | 503.2 | 51.1 | 10 |

TABLE 9b

Classification for combination of cisplatin and MLN4924 in NCI-H82 xenograft model

| Treatment | Synergy score (Day 22) | Synergy score standard error | P-value | Classification |
|---|---|---|---|---|
| 60 mg/kg MLN4924 BID Q2Dx3/week; 4 mg/kg cisplatin | −57 | 14.1 | 0.001 | synergy |
| 60 mg/kg MLN4924 BID Q3Dx2/week; 4 mg/kg cisplatin | −25.4 | 13.4 | 0.072 | additive |
| 60 mg/kg MLN4924 BID Q2Dx3/week; 2 mg/kg cisplatin | −12 | 11.8 | 0.319 | additive |
| 60 mg/kg MLN4924 BID Q3Dx2/week; 2 mg/kg cisplatin | 9.7 | 9.4 | 0.312 | additive |

What is claimed is:

1. A method of treating a solid tumor, comprising administering to a patient in need of such treatment a combination of: ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or a pharmaceutically acceptable salt thereof; and
carboplatin;
wherein the solid tumor is lung cancer.

2. The method of claim 1, wherein the ((1S,2S,4R)-4-(4-((1S)-2,3-dihydro-1H-inden-1-lylamino)-7H-pyrrolo[2,3-d]pyrimidin-7-yl)-2-hydroxycyclopentyl)methyl sulfamate or a pharmaceutically acceptable salt thereof is administered on each of days 1, 3, and 5 of a 21 day schedule.

3. The method of claim 2, wherein the amount of ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or a pharmaceutically acceptable salt thereof administered on each of days 1, 3, and 5 of a 21 day schedule is less than or equal to 50 mg/m$^2$.

4. The method of claim 1, wherein the lung cancer is non-small cell lung cancer.

5. The method of claim 3, wherein the amount of ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or a pharmaceutically acceptable salt thereof administered on each of days 1, 3, and 5 of a 21 day schedule is less than or equal to 25 mg/m$^2$.

6. The method of claim 3, wherein the amount of ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or a pharmaceutically acceptable salt thereof administered on each of days 1, 3, and 5 of a 21 day schedule is less than or equal to 20 mg/m$^2$.

7. The method of claim 1, wherein the carboplatin is administered on day 1 of a 21 day schedule.

8. The method of claim 1, wherein a HCl salt of ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate is administered.

9. The method of claim 7, wherein the amount of carboplatin administered on day 1 of a 21 day schedule is AUC 5 or AUC 6.

10. The method of claim 7, wherein the amount of ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or a pharmaceutically acceptable salt thereof administered on each of days 1, 3, and 5 of a 21 day schedule is less than or equal to 25 mg/m$^2$;
wherein the amount of carboplatin administered on day 1 of a 21 day schedule is AUC 5 or AUC 6.

11. The method of claim 10, wherein a HCl salt of ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate is administered.

12. The method of claim 10, wherein the solid tumor is lung cancer.

13. The method of claim 10, wherein the lung cancer is non-small cell lung cancer.

* * * * *